United States Patent [19]

Pickup et al.

[11] Patent Number: 5,443,964
[45] Date of Patent: Aug. 22, 1995

[54] POXVIRUS INSERTION/EXPRESSION VECTOR

[75] Inventors: David J. Pickup; Dhavalkumar D. Patel, both of Durham, N.C.

[73] Assignee: Duke University, Durham, N.C.

[21] Appl. No.: 84,406

[22] Filed: Aug. 10, 1987

[51] Int. Cl.$^6$ .................. C12N 15/86; C12N 15/11; C12N 5/16; C12P 21/00

[52] U.S. Cl. .................... 435/69.1; 536/24.1; 435/235.1; 435/320.1; 435/240.2; 935/32; 935/34; 935/70

[58] Field of Search ............ 435/68, 70, 172.1, 172.3, 435/235, 240.1, 320, 69.1, 235.1, 320.1, 240.2; 536/27, 23.72, 24.1; 935/6, 7, 32, 34, 57, 65, 70; 424/86, 89; 514/2

[56] References Cited

U.S. PATENT DOCUMENTS

| | | | |
|---|---|---|---|
| 4,419,446 | 12/1983 | Howley et al. | 435/69.1 |
| 4,495,190 | 1/1985 | Curt-Erik et al. | 544/276 |
| 4,495,280 | 1/1985 | Bujard et al. | 435/6 |
| 4,503,142 | 3/1985 | Berman et al. | 435/6 |
| 4,508,826 | 4/1985 | Foor et al. | 435/320.1 |
| 4,510,245 | 4/1985 | Cousens et al. | 435/172.3 |
| 4,511,502 | 4/1985 | Builder et al. | 530/417 |
| 4,511,503 | 4/1985 | Olson et al. | 530/422 |
| 4,511,652 | 4/1985 | Fogel et al. | 435/29 |
| 4,512,922 | 4/1985 | Jones et al. | 530/408 |
| 4,514,497 | 4/1985 | Kit et al. | 435/235.1 |
| 4,517,294 | 5/1985 | Bock et al. | 435/69.4 |
| 4,518,526 | 5/1985 | Olson et al. | 530/351 |
| 4,518,584 | 5/1985 | Mark et al. | 424/85.2 |
| 4,518,690 | 5/1985 | Guntaka | 435/61.4 |
| 4,554,159 | 11/1985 | Roizman et al. | 424/205.1 |
| 4,603,112 | 7/1986 | Paoletti et al. | 435/235.1 |
| 4,745,051 | 5/1988 | Smith et al. | 435/68 |

FOREIGN PATENT DOCUMENTS

| | | | |
|---|---|---|---|
| 127839 | 12/1984 | European Pat. Off. | |
| 155476 | 9/1985 | European Pat. Off. | |
| 198328 | 10/1986 | European Pat. Off. | |
| 0397560 | 11/1990 | European Pat. Off. | C12N 15/86 |
| 1202288 | 8/1989 | Japan | C12N 15/00 |
| 2105344 | 3/1983 | United Kingdom | |
| 8402077 | 6/1984 | WIPO | |

OTHER PUBLICATIONS

Patel et al (1986) Virology 149: 174–189.
Pouwels et al eds in Cloning Vectors (1985) VIII Bbi15.
Hall, R. L. et al. 1991. J. Virology vol. 65 pp. 6516–6527.
Banville, M. et al. 1992. J. Gen. Virology vol. 73 pp. 559–566.
Hall, R. L. et al. 1993. Virology vol. 192 pp. 179–187.
Boyle, D. B. et al. 1988. *Virus Research* vol. 10 pp. 343–356.
Esposito, J. J. et al. 1988. *Virology* vol. 165 pp. 313–316.
Simonsen, C. C. et al. 1983, Molecular and Cellular Biology vol. 3 pp. 2250–2258.
Antczak, J. B. et al. 1992, Proc. Natl. Acad. Sci. USA vol. 89 pp. 12033–12037.
Patel, D. D. et al, 1987, EMBO Journal vol. 6 pp. 3787–3794.
Boyle et al, "Identification and Cloning of the Fowlpox Virus Thymidine Kinase Gene Using Vaccinia Virus", *J. Gen. Virol.* 67:1591–1600 (1986).
Chakrabarti, et al, "Vaccinia Virus Expression Vector: Coexpression of B-Galactosidase Provides Visual Screening of Recombinant Virus Plaques", *Mol. Cell. Biol.* 5:3403–3409 (1985).

(List continued on next page.)

*Primary Examiner*—Mary E. Mosher
*Attorney, Agent, or Firm*—Nixon & Vanderhye

[57] ABSTRACT

The invention comprises a plasmid vector, utilizing genetic material that causes high levels of expression of poxvirus genes, and the method of using this genetic material. One preferred embodiment comprises an upstream cis-acting element of a poxvirus gene encoding the major protein component of the poxvirus A-type inclusion. A second preferred embodiment of the invention comprises a downstream cis-acting element of a poxvirus gene encoding the major protein component of the poxvirus A-type inclusion. These elements are inserted upstream and downstream respectively, of selected cloned genes in the plasmid vector to obtain very high levels of expression of the cloned gene.

12 Claims, 10 Drawing Sheets

OTHER PUBLICATIONS

Doerfler, "Expression of the *Autographa californica* Nuclear Polyhedrosis Virus Genome in Insect Cells: Homologous Viral and Heterologous Vertebrate Genes-The Baculovirus Vector System", *Current Topics in Microbiol. Immunol.* 131:51–68 (1986).

Kitamoto et al, "Polypeptide Analysis with Monoclonal Antibodies of A Type Inclusion Bodies Included by Cowpox Virus", *Arch. Virol.* 89:15–28 (1986).

Langridge et al, "Structural Proteins of *Amsacta moorei, Euxoa auxiliaris,* and *Melanoplus sanguinipes* Entomopoxviruses", *J. Invert. Pathol* 39:346–353 (1982).

Mackett et al, "Vaccinia Virus Expression Vectors", *J. Gen. Virol.* 67:2067–2082 (1986).

Mackett et al, "Vaccinia virus; A Selectable Eukaryotic Cloning and Expression Vector", *Proc. Natl. Acad. Sci. USA.* 79:7415–7419 (1982).

Macket et al, "General Method for Production and Selection of Infectious Vaccinia Virus Recombinants Expressing Foreign Genes", *J. Virol.* 49:857–864 (1984).

Panicali et al, "Construction of Poxviruses as Cloning Vectors: Insertion of the Thymidine Kinase Gene from Herpes Simplex Virus into the DNA of Infectious Vaccinia Virus", *Proc. Natl. Acad. Sci. USA* 79:4927–4931 (1982).

Patel et al, "Isolation of Cowpox Virus A-Type Inclusions and Characterization of Their Major Protein Component", *Virology* 149:174–189 (1986).

Pennock et al, "Strong and Regulated Expression of *Escherichia coli* B-Galactosidase in Insect Cells with a Baculovirus Vector", *Mol. Cell. Biol.* 4:399–406 (1984).

Post et al, "A Generalized Technique for Deletion of Specific Genes in Large Genomes: Alpha Gene 22 of Herpes simplex Virus 1 is Not Essential for Growth", *Cell* 25:227–232 (1981).

Rigby, "Cloning Vectors Derived from Animal Viruses", *J. Gen. Virol.* 64:255–266 (1983).

Smith et al, "Production of Human Beta Interferon in Insect Cells Infected with a Baculovirus Expression Vector", *Mol. Cell. Biol.* 3:2156–2165 (1983).

Smith et al, "Vaccinia Virus Expression Vectors: Construction, Properties and Applications", *Bio Techniques* Nov./Dec. 306–312 (1984).

Fig. 1

```
    GAATTCATGCTATAAGACTCATCAACGATAGTACTGATGCTCAACATATACATTTTGGAT
  1                                                              60
      I  H  A  I  R  L  I  N  D  S  T  D  A  Q  H  I  H  F  G  F -

TTAGAAATATGGTAATAATAGACAATGAATGCGCTAATATTCAGTCAAGTGCTGAAAATG
 61                                                             120
      R  N  M  V  I  I  D  N  E  C  A  N  I  Q  S  S  A  E  N  A -

CAACTGATACAGGACATCATCAAGATAGCAAAATAAATATCGAAGTTGAAGATGATGATG
121                                                             180
      T  D  T  G  H  H  Q  D  S  K  I  N  I  E  V  E  D  D  D  D -

ATGATGATGATGATGATGATGATGATGATGATGATGATGATGATGATGATGATGATGATG
181                                                             240
      D  D  D  D  D  D  D  D  D  D  D  D  D  D  D  D  D  D  D  D -

ATGATGATGATGATGTCATAGACGATGATGATTATAATCCAAAACCCACTCCGATACCGG
241                                                             300
      D  D  D  D  V  I  D  D  D  D  Y  N  P  K  P  T  P  I  P  E -

AGCCTCACCCTAGACCACCGTTTCCCAGACATGAATATCATAAGAGGCCGAAAGTTCTTC
301                                                             360
      P  H  P  R  P  P  F  P  R  H  E  Y  H  K  R  P  K  V  L  P -

CTGTAGAAGAACCTGATCCTGTCAAAAAAGACGCGGATCGTATAAGACTTGATAATCATA
361                                                             420
      V  E  E  P  D  P  V  K  K  D  A  D  R  I  R  L  D  N  H  I -

TATTAAACACATTGGATCATAATCTTAATTCCATCGGACACTATTGTTGTGATACAGCAG
421                                                             480
      L  N  T  L  D  H  N  L  N  S  I  G  H  Y  C  C  D  T  A  A -

CAGTTGATAGGTTAGAACATCACATTGAAACATTGGGACAATATGCAGTAATACTAGCAA
481                                                             540
      V  D  R  L  E  H  H  I  E  T  L  G  Q  Y  A  V  I  L  A  R -

GAAAGATAAATATGCAAACATTACTGTTCCCATGGCCATTACCTACTGTCCATCCACATG
541                                                             600
      K  I  N  M  Q  T  L  L  F  P  W  P  L  P  T  V  H  P  H  A -

CGATAGATGGTAGTATTCCGCCACATGGGAGATCTACGATCTTATAATTACACGATTGTA
601                                                             660
      I  D  G  S  I  P  P  H  G  R  S  T  I  L

GTTAAGTTTTGAATAAAATTTTTTTATAATAAATGGAGGTCACGAACCTTATTGAAAAAT
661                                                             720
                                      M  E  V  T  N  L  I  E  K  C -

GTACCAAGCACTCCAAAGATTTCGCCACTGAGGTAGAAAAACTATGGAACGATGAGTTGA
721                                                             780
      T  K  H  S  K  D  F  A  T  E  V  E  K  L  W  N  D  E  L  S -

GTTCTGAATCAGGTCTCTCAAGAAAAACAAGAAATGTAATTCGTAATATTCTTCGTGATA
781                                                             840
      S  E  S  G  L  S  R  K  T  R  N  V  I  R  N  I  L  R  D  I -

TCACTAAGTCACTAACTACAGATAAGAAATCAAAGTGTTTCCGTATACTAGAACGTTCGA
841                                                             900
      T  K  S  L  T  T  D  K  K  S  K  C  F  R  I  L  E  R  S  T -

CGATTAACGGAGAGCAGATTAAAGATGTATATAAAACTATTTTTAATAATGGTGTTGATG
901                                                             960
      I  N  G  E  Q  I  K  D  V  Y  K  T  I  F  N  N  G  V  D  V -

TGGAGTCTAGAATCAACACTACAGGAAAGTATGTTCTATTTACAGTTATGACTTATGCTG
961                                                            1020
      E  S  R  I  N  T  T  G  K  Y  V  L  F  T  V  M  T  Y  A    -

Alu 1

AGC TTC GTC TTT TTA CCT CTA CAT CTA ACG GTT GCC
TTG TCC TGA GTT AAA TGC CTC AGA CGC AAG TAA TAA
ATT GGT CCA AAA AAT ACT TTG GAT GCA TAA GGC TTA
TCC GTT TCA GGA TCA TAG AGA ATC TTT TCA CAA AAG
ATT TTA TCC GAT AAT TCT TCA TCA GAC AAT TTC GGA
TTT GAA TGC TCA TAA CAT TGT TTA GCG AAT TGC ATA
TAT GTA TCG ATG GAT GTT TCG TTA CTA CTA GGA AAA
CAG ACA GGT CGG TTT TCT CCC TTA TTG TTG TAC GGC
TTA GCA GAA TAT GCG GCT GTT AAA ATA ACT TCT ATC
AAC ATA GAT ATA GTT TTT CTA GA

Xba 1

POXVIRUS INSERTION/EXPRESSION VECTOR

FIELD OF THE INVENTION

This invention relates to the following: (1) a vector for cloning and expressing cloned DNA sequences; and (2) to methods for making and using this vector. In particular, the invention pertains to use of cis-acting elements derived from those directing the unusually high level of expression of a gene of the cowpox virus. These elements are used to obtain high levels of expression of the genetic material inserted into poxvirus expression vectors.

BACKGROUND INFORMATION

Poxviruses. The cowpox virus is a member of the poxviridae, the poxvirus family, a large group of DNA-containing animal viruses. The classification and nomenclature of the poxviruses is described by Matthews, *Intervirology* 17: 42–46 (1982). The disclosure of this reference and all others cited in the background information and in the discussion of the invention are incorporated by reference herein. The poxviridae comprises two subfamilies: the chordopoxvirinae (poxviruses of vertebrates) and the entomopoxvirinae (poxviruses of insects). The poxviruses all have many similar structural, enzymatic, and genetic properties. They all replicate in the cytoplasm within viral "factories" (Cairns, *Virology* 11: 603–623 (1960)), also termed B-type cytoplasmic inclusions (Kato et al., *Biken's J.* 2: 353–363 (1959)).

In addition to the B-type cytoplasmic inclusions, many poxviruses produce large proteinaceous cytoplasmic inclusion bodies. Examples of chordopoxvirinae producing such inclusions (referred to as A-type inclusion bodies or ATIs) include the following: (1) Genus orthopoxvirus, ectromelia virus (Marchal, *J. Pathol. Bacteriol.* 33: 713–728 (1930)); cowpox virus (Downie, *J. Pathol. Bacteriol.* 48: 361–379 (1939)); (2) Genus parapoxvirus: bovine pustular stomatitis virus (Naginton, *Vet. Rec.* 82: 477–482 (1968)); (3) Genus avipoxvirus: fowlpox virus and canary poxvirus (Kato and Cutting, *Stanford Med. Bull.* 17: 34–45 (1959)); (4) Genus capripoxvirus: goatpox virus (Tantawi and Al Falluji, *Acta Virol.* 23: 455–460 (1979)); and (5) Genus suipoxvirus: swinepox virus (Teppema and DeBoer, *Arch. Virol.* 49: 151–163 (1975)). The possibility that members of the genus leporipoxvirus (rabbit myxoma and rabbit fibroma viruses) produce ATIs is discussed by Kato and Cutting, *Stanford Med. Bull.* 17: 34–45 (1959). Examples of entomopoxvirinae that produce proteinaceous cytoplasmic inclusion bodies (in addition to the B-type inclusions) are described by Bergoin and Dales, in *Comparative Virology*, eds. K. Maramorosch and E. Kurstak, 169–205, Academic Press, New York and London (1971).

Of all the poxviruses, those that have been studied most are those belonging to the genus orthopoxvirus (reviewed by Moss, *Virology*, ed. B. N. Fields, 685–703, Raven Press, New York (1985)). This genus includes vaccinia virus (the type species of the genus), cowpox virus, ectromelia virus, monkeypox virus, variola virus and raccoonpox virus. Studies on these viruses have provided the following general information on poxviruses.

The Expression of Poxvirus Genes. The DNA of vaccinia virus is about 180 kb long. It contains about 100 genes that are expressed before the onset of viral DNA replication ("early" genes), and it contains over 50 genes that are expressed after the onset of viral DNA replication ("late" genes). In addition to this temporal regulation of gene expression, the level of expression of each gene is regulated. The mechanisms that effect the temporal and quantitative regulation of expression of viral genes are poorly understood.

The transcription of each viral gene is tightly regulated, and this provides one mechanism of controlling viral gene expression. Viral proteins and specific viral cis-acting elements are required to effect the transcription of poxvirus genes (Puckett and Moss, *Cell* 35: 441–448 (1983); Cochran et al., *Proc. Natl. Acad. Sci. USA* 82: 19–23 (1985)), but little is known about them.

The early genes of vaccinia virus appear to have transcriptional promoter elements that comprise 30–40 bp upstream of the transcriptional start-site (Cochran et al., *J. Virol.,* 54: 30–37 (1985); Weir and Moss, *Virology* 158: 206–210 (1987)). These elements do not resemble the transcriptional control elements of the genes of eukaryotes. The transcription of each gene is terminated 50–70 bp downstream of a thymidine-rich region in the non-transcribed strand of the viral DNA (Rohrman et al., *Cell* 46: 1029–1035 (1986)). Thus, the mRNAs of the early genes are a defined length. In addition, each is capped at its 5'-end, and each contains a poly(A)(adenine) tail of about 100 residues at its 3'-end.

The late genes of vaccinia virus do not appear to have transcriptional promoter elements that are similar either to those of the early genes, or to the genes of eukaryotes. The putative promoter elements of those late genes that have been characterized appear to be short (15–30 bp) sequences located immediately upstream of the end-point of complementarity between the mRNA and the DNA template (Cochran et al., *J. Virol* 54: 30–37 (1985)). This end-point may correspond to both the 5'-end of the mRNA and the transcriptional start-site. Alternatively, there is some evidence that the mRNAs of at least a few late genes contain either 5'-terminal poly(A) sequences or both poly(A) and additional nucleotide sequences at the 5'-end that are not complementary to the corresponding region of the template strand of the viral DNA (Bertholet et al., *Cell* 50: 153–162 (1987); Schwer et al., *Cell* 50: 163–169 (1987); Patel and Pickup, unpublished data). The unusual structures of the 5'-ends of these late mRNAs suggests that the transcription of poxvirus late genes might occur by a novel mechanism. The nature of this mechanism has not yet been determined.

The mRNAs of all previously characterized late genes of vaccinia virus also differ from mRNAs of early genes in that they do not appear to have defined 3'-ends and they are thus not uniform in length (Cooper et al., *J. Virol.* 37: 284–294 (1981); Mahr and Roberts, *J. Virol.* 49: 510–520 (1984); Weir and Moss, *J. Virol.* 51: 662–669 (1984)). The significance of differences between the early and late mRNAs with respect to the structures of their 5'- and 3'-termini is currently unclear. One possible function of the structures of the termini of late mRNA is to enhance the stability of the mRNA. Both 5'- and 3'-end structures can affect the stability of an mRNA (see review by Brawerman, *Cell* 48: 5–6 (1987)). In addition, the sequence flanking the initiation codon in the mRNA may exert a strong influence on the efficiency with which that mRNA is translated (Kozak, *Cell* 44: 283–292 (1986)). Therefore, the structures at each end of an mRNA are likely to affect the amount of gene product synthesized from that mRNA.

Poxvirus-derived Expression Vectors. Animal viruses of several types, including the poxviruses, have been used to construct virus vectors that can direct the expression of cloned genes (for a review, see Rigby, *J. Gen. Virology* 64: 255–266 (1983)). Each virus vector system has its advantages and disadvantages, as discussed in more detail below.

Most of the work on poxvirus-derived vectors has been done with vaccinia virus. Several vaccinia virus vectors are currently in use; these vectors and their applications are reviewed by Mackett and Smith, *J. Gen. Virology* 67: 2067–2082 (1986). The patent of Paoletti and Panicali (U.S. Pat. No. 4,603,112) discloses methods of inserting cloned genes into the genome of vaccinia virus such that the virus can direct the expression of the cloned gene. Methods of inserting cloned genes into the genomes of large DNA-containing viruses are also described by Roizman and Lang, U.S. Pat. No. 4,554,159; Stunnenbe and Wittek, Eur. Pat. No. 198,328; Post and Roizman, *Cell* 25: 227–232 (1981); Mackett, Smith and Moss, *Proc. Natl. Acad. Sci. USA* 79: 7415–7419 (1982); Panicali and Paoletti, *Proc. Natl. Acad. Sci. USA:* 79: 4927–2932 (1982); and Mackett, Smith and Moss, *J. Virol.* 49: 857–864 (1984).

The advantages of poxvirus-derived expression vectors include the following:

1) Various poxviruses replicate in a wide variety of animals. Most importantly, many of them replicate in humans, other mammals or animals that are of economic importance. Some poxviruses such as vaccinia virus have a broad host range; they are capable of replicating in a variety of tissues in several different animals. This allows wide use of the vectors obtained from these poxviruses. Some of the other poxviruses are limited in their replication to certain hosts or to certain cell types. This may be a useful attribute, particularly when it is desirable to restrict a virus infection either to a specific animal or to specific cells. The fact that several poxviruses are able to replicate in localized regions of the skin of certain animals, without producing other serious effects on the animal provides a simple method of raising antibodies against the protein encoded by the cloned gene. Furthermore, this feature has stimulated the development of candidate, live, poxvirus-derived vaccines against several (non-poxvirus) pathogens. Most of these candidate vaccines are expression vectors derived from the strain of vaccinia virus used to vaccinate against smallpox virus. Each contains at least one gene cloned from the targeted pathogen. The aim is to construct virus vectors that will direct the synthesis of enough product of the cloned gene to stimulate the production of sufficient antibody against this protein to protect the inoculated animal from subsequent infection with the pathogen. If successful, humans and other animals might be immunized in this way against a variety of pathogenic agents.

2) The genomes of most poxviruses contain large amounts of genetic information that may be experimentally replaced by other cloned genes. In addition, large amounts of DNA can be inserted within the genomes of poxviruses without any adverse effects. For example, Smith and Moss, *Gene* 25: 21–28 (1983), obtained a viable vaccinia virus recombinant whose DNA contained an insert of 25 kbp of phage lambda DNA. Therefore, unlike many of the other virus-derived expression vectors, the poxvirus-derived vectors are capable of containing relatively large inserts that might contain several cloned genes.

3) Expression of the cloned gene may be delayed until late in the virus multiplication cycle. A cloned gene may be placed under the control of regulatory elements derived from those controlling the expression of a late viral gene. This may be useful if the product of the cloned gene is toxic to the cell. If the cloned gene is only expressed late, then some progeny virus will be produced before the cell is killed by the toxic gene product. This allows the production of some viable recombinant viruses containing the cloned gene, whereas the use of regulatory elements derived from an early gene might result in the production of gene products that kill the cell before viable recombinant viruses are produced.

The disadvantages of poxvirus-derived expression vectors for some uses include the following:

1) Most poxviruses produce a lytic infection resulting in the death of the infected cell. Consequently, the production of the protein encoded by the cloned gene is limited by the lifespan of the infected cell.

2) Poxvirus-derived expression vectors that are currently in use have not been able to direct the synthesis of large amounts of protein. Thus, a significant advantage of this invention over the known prior art is that the vector of the invention provides a way to direct the synthesis of very large amounts of protein by selection of certain cis-acting elements of poxviruses. This is important if the object of using the system is either to recover the purified gene product or to revaccinate an animal that has already been immunized by means of a poxvirus-derived vaccine. The latter situation might arise either if a continued course of immunizations (over a period of months or years) is needed, or if multiple vaccinations are required with poxvirus-derived vectors directing the expression of different cloned genes.

Not only are current poxvirus vectors subject to the disadvantage of low protein synthesis levels, but also few other eukaryotic virus expression vectors are able to direct high levels of expression of a cloned gene. Currently, in this regard, the most successful vector system is that of the baculovirus-derived expression vector system (see review by Doefler, *Curr. Top. Microbiol Immunol.* 131: 51–68 (1986)); Smith et a.l., *Mol. Cell. Biol.* 3: 2156–2165 (1983); Pennock et al; *Mol. Cell. Biol.* 4: 399–406 (1984)). Baculoviruses, which are not poxviruses, are viruses that replicate exclusively in insects. They produce crystalline proteinaceous inclusions bodies (polyhedra) in either the nuclei or the cytoplasm of the host cell. The use of the baculoviruses as expression vectors employing the transcriptional promoter element of the gene encoding the protein component of the nuclear inclusion bodies is disclosed in Smith and Summers, Eur. Pat. No. 127,839 and Miller, Eur. Pat. No. 155,476. Although these baculovirus-derived vector systems have achieved high levels of expression of several cloned genes, they have the disadvantage that this expression can only be obtained in cells derived from insects. Proteins produced in such cells might not be processed in the same way that they would be processed in mammalian cells. Furthermore, the baculovirus-derived vectors cannot be used, as can poxvirus-derived vectors, to raise antibodies against the product of a cloned gene. Therefore, although baculovirus-derived expression vectors are useful and capable of producing high levels of gene expression, they cannot provide some of the functions that poxvirus-derived expression vectors can, most notably, the ability to express cloned genes in mammalian cells.

As noted above, the genes of poxviruses appear to possess regulatory signals that are unlike those of genes of eukaryotes. Therefore, these signals cannot simply be replaced by strong eukaryotic promoter elements in order to gain high levels of gene expression. Instead, one option is to use control elements derived from a poxvirus gene that is strongly expressed. Usually, the most strongly expressed genes of a virus are the late genes many of which encode the major protein components of the virus particle. The putative promoter elements of some of these genes have been used in poxvirus-derived expression vectors (Mackett et al., *J. virol* 49: 857–864 (1984); Chakrabarti et al, Mol. Cell. Biol. 5: 3403–3409 (1985)), but the levels of gene expression obtained with these elements have been only moderate. The preferred embodiment of this invention utilizes one of the most strongly-expressed of all poxvirus genes, that encoding for the major protein component of the poxvirus A-type inclusion bodies (see below and Patel et al., *Virology* 149: 174–189 (1986), to gain high levels of expression of genes cloned into poxvirus-derived expression vectors. The vector of this invention is one in which the synthesis of cloned genes' mRNAs is placed under the control of the cis-acting elements derived from a gene directing the production of the mature mRNA encoding a poxvirus A-type inclusion protein.

A-type Inclusions. A-type inclusions or ATIs are large, well-defined, proteinaceous bodies, that are encoded by the viral genome and produced in the cytoplasm of cells late in the viral multiplication cycle of many poxviruses. Depending on the particular poxvirus strain, ATIs may or may not contain virus particles. In infected cell cultures, mature cowpox virus particles begin to appear at 4–5 hours after infection and readily detectable ATIs begin forming 8–9 hours after infection. Virus progeny are contained within the ATIs in some of the cowpox strains. ATIs are produced in almost all cells infected by cowpox viruses. Patel et al., *Virology* 149: 174–189 (1986) showed that the major component of ATIs produced in cells infected with cowpox virus is a protein having a molecular weight of about 160 kilodaltons (kDa). During the late stages of infection, this protein may comprise up to 4% of the total cellular protein but is not a part of the virus structure itself. This is an unusually large amount of a viral protein; most of the 100–200 viral proteins including the major structural proteins each comprise much less than 1% of the total cell protein. Consequently, they are not readily detectable against the background of cellular proteins when total proteins of infected cells are examined by Coomassie blue staining of proteins resolved by polyacrylamide gel electrophoresis. In contrast, the 160 kDa ATI protein of cowpox virus is easily detectable (Patel et al., *Virology* 14: 176–189 (1986).

Antibody raised against purified 160 kDa ATI protein of cowpox virus reacts specifically with the following abundant late proteins: a 155 kDa protein in cells infected with raccoonpox virus; a 94 kDa protein in cells infected with vaccinia virus; a 130 kDa protein in cells infected with ectromelia virus; and a 92 kDa protein in cells infected with monkeypox virus (Kitamoto et al., *Arch. Virol.* 89: 15–28 (1986); Patel et al., *Virology* 149: 174–189 (1986); J. Esposito, D. Patel, and D. Pickup, unpublished results).

Therefore, representative orthopoxviruses of all types (with the possible exception of variola virus, which was not tested) direct the synthesis of a protein that is antigenically related to the 160 kDa ATI protein of cowpox virus. These proteins appear to be the products of genes related to the ATI gene (Esposito, Patel and Pickup, unpublished results). The smaller of these gene products (those of vaccinia virus and monkeypox virus) do not appear to aggregate into typical ATI structures.

Antibody directed against the purified 160 kDa ATI protein has not yet been used to probe the antigenic relatedness between the ATIs of the chordopoxvirinae and the proteins of the cytoplasmic inclusions produced by entomopoxviruses; however, it is noteworthy that Langridge and Roberts, *J. Invert. Path.* 39: 346–353 (1982) estimated the molecular mass of the protein component of an entomopoxvirinae cytoplasmic inclusion to be about 110 kDa, similar to the molecular mass of the ATI inclusion protein of cowpox virus.

The Gene Encoding the Major Protein Component of the A-Type Inclusions Produced by the Cowpox Virus. The major protein component of the ATIs produced by the Brighton red strain of cowpox virus is a 160 kDa protein (Patel et al., *Virology* 149: 174–189 (1986)). This protein appears to be one of the most abundant of all viral proteins in the cell. The gene encoding the 160 kDa ATI protein has been identified and characterized and has been designated the 160K gene (Patel and Pickup, manuscript submitted (1987)). This gene is contained within the Kpn I G fragment of the DNA of the Brighton red strain of cowpox virus (see FIG. 4). The transcribed portion of this gene is shown in this figure.

The nucleotide sequences at each end of the transcribed region of the 160K gene have been determined. The sequence containing the initiation codon of the 160K gene is shown in FIG. 1. This sequence contains the regulatory elements necessary to direct the tranhscription of the 160K gene. This upstream sequence from the 160K gene sequence will be referred to as cis-acting element I or CAE I. The most unusual feature of this sequence is the presence of 28 consecutive repeats of the triplet GAT (nucleotides 171–254). The significance of these repeats is currently unclear. The nucleotide sequence at the other end of the 160K gene, shown in FIG. 2, contains the nucleotide sequence corresponding to that at the end of the complementarity between the 3'-end of the 160K gene's mRNA and the template strand of the viral DNA (see FIG. 8). This downstream sequence from the 160K gene sequence will be referred to as cis-acting element II or CAE II.

Unlike the other characterized late mRNAs of poxviruses, which appear to have heterogeneous 3'-ends (Cooper et al., *J. Virol.* 37: 284–294 (1981); Mahr and Roberts, *J. Virol.* 49: 510–520 (1984); Weir and Moss, *J. Virol.* 51: 662–669 (1984)), the 160K gene's mRNAs are uniform in length.

In addition, some characterized late mRNAs of genes of vaccinia virus appear to have heterogeneous 5'-ends as well as heterogeneous 3'-ends. Bertholet et al., *Cell* 50: 153–162 (1987) have reported that the late mRNA of a late gene (11K gene) of vaccinia virus contains leader sequences that may be up to thousands of nucleotides long. These leaders appear to be derived from different regions of the viral genome and to be linked to the coding region of the late gene via a poly(A) sequence immediately upstream of the initiation codon. In contrast, Schwer et al., *Cell* 50: 163-169 (1987), reported that mRNAs of the same 11K gene contained only poly(A) leaders that were about 35 residues long.

The 5'-termini of the mRNA of the 160K gene of cowpox virus each contain a poly(A) leader sequence immediately upstream of the initiation codon. Most of these mRNAs contain leaders of between 5 and 20 A residues (Patel and Pickup, manuscript submitted, 1987). These 5'-terminal poly(A) sequences are not complementary to the corresponding region of the template strand of the viral DNA. It is not yet clear how these 5'-terminal poly(A) containing mRNAs are produced.

The function of the poly(A) leader sequence is also unknown. This structure may enhance the translational efficiency of the mRNA. Kozak (*Cell* 44: 283-292 (1986)) demonstrated that the presence of a purine residue three nucleotides upstream of an initiation codon would exert a dominant positive effect on the efficiency of translation from that initiation codon. The poly(A) tract provides a purine at the appropriate position. The effect of the remainder of the poly(A) leader sequence on translational efficiency is unknown.

Another possible function of the 5'-poly(A) leader might be to increase the stability of that mRNA. During the multiplication of vaccinia virus the cellular mRNAs are degraded at a greater rate than mRNAs in uninfected cells; however, the viral mRNA appears to be less susceptible than cellular mRNAs to the virus-induced RNA degradation (Rice and Roberts, *J. Virol.* 47: 529-539 (1983)). The 5'-terminal poly(A) sequences may contribute to the stability of the late viral mRNAs, thereby potentially increasing the pool of mRNA that is available for translation.

As noted above, the mRNAs of the 160K gene have one other unusual structural feature. Each has a defined 3'-end that corresponds to a position just downstream of the 160K gene's open reading frame (Patel and Pickup, manuscript submitted (1987)). It is not yet clear how these mRNAs+ defined 3'-ends are generated. They may be produced either by the termination of transcription at a specific site, or by RNA processing of some description. Whatever the mechanism, the sequence (CAE II) shown in FIG. 2 is sufficient to direct the production of defined 3'-ends. For example, when this sequence element was placed downstream of a cloned gene under the control of CAE I (see example VII), it directed the production of mRNAs that contained defined 3'-ends, whereas if the CAE II was absent, the 3'-ends of the mRNAs were heterogeneous in length.

The significance of the defined 3'-ends of the 160K gene's mRNAs is unknown. It is a feature that is unusual and perhaps unique among the late viral mRNAs. Therefore, it too may contribute to the unusually high level of expression of the 160K gene. Again, one possible mechanism by which it may exert such an effect is by increasing the stability of the mRNA, because the structure of the 3'-end of a mRNA can govern the rate at which that mRNA is degraded (for a recent review on the rate of decay of mRNAs, see Brawerman, *Cell* 448: 5-6 (1987)).

The use of a downstream cis-acting element inserted into a vector downstream of a cloned gene has not been found in the prior art. In this invention, use of a downstream cis-acting element derived from a gene encoding for a major A-type inclusion protein produces late mRNAs that have defined 3'-ends.

In summary, the 160K gene encoding the major protein component of the ATIs produced by cowpox virus appears to be one of the most strongly-expressed genes of this virus. This gene and its counterparts in the genomes of poxviruses of other types may prove to be the most strongly-expressed of all poxvirus genes. Accordingly, the features that effect such high levels of expression of these genes may provide the best means of directing high levels of expression of genes cloned into poxvirus-derived vectors. We have identified and characterized the cis-acting elements (CAE I and CAE II) that direct the synthesis of the mRNA of the 160K gene, and also determined the structures of the 5'- and 3'-ends of these mRNAs. We have modified these elements and used them to direct high levels of expression of genes cloned into poxvirus-derived vectors.

SUMMARY OF THE INVENTION

The vector of this invention is derived from the cis-acting elements that control the transcription of a very strongly-expressed poxvirus gene. These cis-acting elements do not closely resemble other cis-acting elements that are currently used to control the transcription of cloned genes in vectors. Furthermore, it appears that these other cis-acting elements do not function as well as the cis-acting elements of the invention in enabling the production of the products of the genes associated with the sequences.

The invention comprises: (1) plasmid vectors containing cis-acting elements derived from what appears to be the most strongly-expressed gene of a poxvirus such as the cowpox virus; and (2) a method for using these cis-acting elements in order to gain high levels of expression of genes inserted into poxvirus-derived vectors.

The plasmid vectors contain cis-acting elements derived from those directing the production of the mature mRNAs of the 160K gene of cowpox virus. This gene encodes the 160 kDa protein that is the major component of the A-type inclusions produced in cells infected with cowpox virus. These vectors have been designed to allow for simple insertion of cloned genes such that the poxvirus-derived cis-acting elements direct the production of mRNAs of these cloned genes. The preferred embodiments of the invention, containing CAE I (p1200) and CAE II (p1277) were deposited in accord with the Budapest Convention on Jul. 28, 1987, and are available to the public at the American Type Culture Collection, Rockville, Md., as ATCC No. 40355 and ATCC No. 40356, respectively.

This invention has the advantages available through use of poxvirus vectors as discussed above, in addition to embodying the advantages due to employment of the cis-acting elements of this strongly expressed gene, the ATI protein gene. Such advantages include the use of poxviruses containing the vector as a live vaccine. The previous use of many different recombinant poxviruses containing diverse expression vectors as live vaccines makes it clear that the recombinant poxvirus of the invention, containing the cis-acting elements, may also be used as a live vaccine (see, for example, Moss and Smith, PCT Application 84/02077) and Paoletti et al., U.S. Pat. No. 4,603,112).

The disclosure of this invention enables use of the very productive vectors of the invention for obtaining high levels of antibodies to the product of the selected cloned genes. The advantage of using a vector enabling high levels of production of the gene product is that the recipient of the live vaccine is likely to be better immunized with a longer-lasting immunity than the recipient of a live vaccine that does not direct such high levels of production of the gene product. Because orthopoxviruses infect mammalian cells they can be used for live vaccines that target mammalian cells. Similarly, for example, the use of the fowlpox virus and the appropriate ATI cis-acting elements allows preparation of live vaccines for fowl hosts using the vector and methods of the invention. Although not formally proven, it is likely that the cis-acting elements controlling the transcription of the 160K gene of cowpox virus will function within the genomes of a wide variety of poxviruses. The Examples given in this application demonstrate that these cowpox virus derived elements function within the genome of another orthopoxvirus, namely vaccinia virus. Additional evidence that cis-acting transcriptional control elements of a poxvirus will function in the genome of a different poxvirus is provided by Boyle and Coupar, *J. Gen. Virol.* 67: 1591–1600 (1986), who showed that the elements controlling the transcription of the thymidine kinase gene of fowlpox virus (Genus, Avipoxvirus) appeared to function when placed into the genome of vaccinia virus (Genus, Orthopoxvirus). Therefore, this invention should find application in poxviruses of most genera.

It is, therefore, one object of the invention to provide a means to obtain high levels of expression of selected genetic material. It is also an object of the invention to obtain this high level of expression within specific mammals, specific mammalian cells or other animals or tissues. It is another object of the invention to provide a means to obtain enhanced immunity to a particular antigen by increasing production of the antigen.

BRIEF DESCRIPTION OF THE DRAWINGS

FIG. 1 is the nucleotide sequence of the region flanking the initiation codon (ATG) of the 160K gene. Shown is the sequence of 1021 nucleotides of an EcoR I-Fnu4HI segment of the Kpn I G fragment of CPV DNA. The initiation codon of the 160K gene is at nucleotide 693. This sequence will be referred to as cis-acting element I or CAE I. The position of this element within the genome of the Brighton red strain of cowpox virus is shown in FIG. 4.

FIG. 2 is the nucleotide sequence of the 345 bp Alu I-Xba I fragment that directs the production of the defined 3′-ends of the 160K gene's mRNAs. This sequence will be referred to as cis-acting element II or CAE II. The position of this element within the genome of the Brighton red strain of cowpox virus is shown in FIG. 8.

FIG. 3 is shows two restriction maps: A) the Hind III restriction map of the DNA of the western reserve strain of vaccinia virus (Mackett and Archard, *J. Gen. Virol.* 45: 683–701 (1979); DeFilippes, *J. Virol.* 43: 136–169 (1982)); and B) the restriction map of the Hind III J fragment. Restriction enzyme cleavage sites are abbreviated as follows: h, Hind III; c, Cla I; e, EcoR I; and k, Kpn I. The Hind III J fragment was inserted into the Hind III site of plasmid cloning vehicle pUC19 to produce plasmid p1133. In plasmid p1133, the multiple cloning sites within the pUC19-derived DNA are next to the Hind III site that is the closer to the Cla I site in the Hind III J fragment.

FIG. 4 shows the strategy used to clone and modify the cis-acting element I (CAE I) of the 160K gene.

(A) The Kpn I restriction map of the DNA of the Brighton red strain of cowpox virus (Archard et al., *J. Gen. Virol* 65: 875–856 (1984); Pickup et al. *Proc. Natl. Acad. Sci. USA* 81: 6817–6821 (1984)).

(B) A restriction map of the Kpn I G fragment. The arrow depicts the extent of the complementarity between the 160K gene and its mRNA. The direction of the arrow indicates the direction of transcription of this gene; the tail of the arrow corresponds to the 5′-end of the coding region of the 160K gene. This Kpn I fragment is contained in plasmid p2003.

(C) A restriction map of the 6.4 kb Cla I subfragment of the Kpn I G fragment. This Cla I fragment is contained in the plasmid p2025.

(D) A restriction map of the sequence designated cis-acting element I (see FIG. 1).

(E) A restriction map of the 886 bp EcoR I fragment contained in plasmid p2030.

(F) A restriction map of the EcoR I-Hind III fragment (containing the modified CAE I) that is itself contained with plasmid p2046.

Restriction-enzyme cleavage sites are abbreviated as follows: a, Alu I; b, Bgl II; c, Cla I; e, EcoR I; f, Fnu 4H; h, Hind III; k, Kpn I; m, Msp I; n, Nco I; p, Pst I; s, Sal I; t, Tag I; v, EcoR V; and x, Xba I. e[a] denotes that the Alu I site was converted to an EcoR I site. The sites denoted with asterisks (part F) are the sites introduced into the DNA by oligonucleotide-directed mutagenesis.

FIG. 5 shows a restriction map of plasmid p1200. This plasmid consists of the 2.7 kb plasmid cloning vehicle pUC19 containing a 5.5 kb Hind III fragment inserted into its Hind III site. The 5.5 kb Hind III fragment insert is derived from the 5.0 kb Hind J fragment of the DNA of the western reserve strain of vaccinia virus (see FIG. 3). A 533 base-pair Taq I fragment containing the modified cis-acting element I of the 160K gene (see FIG. 4F) has been inserted into the Cla I site of the Hind III J fragment. This regenerated only one Cla I site (that incorporating the Taq I site introduced into the modified CAE I). Thus, the inserted modified CAE I within p1200 directs transcription in a clockwise direction (with respect to this map) from about the position of the Cla I site. The numbers shown in parentheses in this figure indicate the lengths in kilobase-pairs (in a clockwise direction) from the EcoR I site within the pUC19-derived segment of this plasmid.

FIG. 6 shows a restriction map of plasmid p1245. This plasmid consists of plasmid p1200 containing a cloned copy of the Tn9 chloramphenicol acetyltransferase (CAT) gene, that was inserted at the Cla I site. The insertion of the 0.8 kb Taq I fragment containing the chloramphenicol acetyltransferase gene did not regenerate the Cla I site. Transcription of the CAT gene is controlled by CAE I. Numbers in parentheses indicate the lengths in kilobase-pairs (in a clockwise direction) from the EcoR I site within the pUC19-derived segment of this plasmid.

FIG. 7 shows the expression of the CAT gene under the control of the modified CAE I. This figure shows microdensitometer scans of the PAGE-resolved proteins of cells infected with either: (A) wild-type vaccinia virus; or (B) vaccinia virus recombinant A394 (the recombinant containing the CAT gene under the control of CAE I). The cells were infected at multiplicities of 10 pfu/cell. They were harvested 36 hours after infection. The solubilized proteins of these cells were resolved by electrophoresis through 15% polyacrylamide gels, as described in Example VI. The proteins were stained with Coomassie Brilliant blue. The arrows indicate the electrophoretic mobilities of: (1) glutamate dehydrogenase, 55.4 kDa; (2) lactate dehydrogenase, 36.5 kDa; and trypsin inhibitor, 20 kDa. The peak corresponding to the CAT gene product is indicated in panel B.

FIG. 8 shows the strategy used to clone and modify the cis-acting element II (CAE II) of the 160K gene.

(A) The Kpn I restriction map of the DNA of the Brighton red strain of cowpox virus (Archard et al., J Gen. Virol. 65: 875–886 (1984); Pickup et al., Proc. Natl. Acad. Sci. USA 81: 6817–6821 (1984)).

(B) A restriction map of the Kpn I G fragment. The arrow depicts the extent of complementarity between the 160K gene and its mRNA. The direction of the arrow indicates the direction of transcription of this gene; the head of the arrow corresponds to the endpoint of complementarity between the 160K gene and the 3'-ends of its mRNAs. This Kpn I fragment in contained in plasmid p2003.

(C) A restriction map of the 2 kb EcoR I fragment containing the CAE II. This fragment is contained in plasmid p2060.

(D) A restriction map of a 600 bp Alu I fragment containing CAE II. This Alu I fragment was derived from plasmid p2060, and is contained in plasmid p 2070.

(E) A restriction map of CAE II (see FIG. 2). The Alu I sites are in brackets because these sites were not regenerated when the Alu I-generated fragment was ligated into the HinC II site in the pUC19 DNA. This 0.3 kb fragment of DNA was obtained as an Xba I-[Alu I] Xba I fragment of the DNA of plasmid p2070. The Xba I site closer to the [Alu I] site was present in the polylinker cloning site within the pUC19 DNA.

Subsequently, this 0.3 kb Xba I fragment was inserted into the Xba I site within the DNA of plasmid p2050. This placed a BamH I site next to each Xba I site.

The CAE II element (modified by the addition of BamH I sites to each end) was purified and then inserted into the BamH I site in the DNA of plasmid p1275 (FIG. 6). The map of the product (p1277) containing the CAE II element in the appropriate orientation relative to the CAT gene is shown in FIG. 9. Restriction enzymes site are abbreviated as described in FIG. 4. In addition, the Dde I sites are abbreviated to d.

FIG. 9 shows a restriction map of plasmid p1277. Plasmid p1277 is similar to plasmid p1245 (FIG. 6). However, all the restriction sites in the polylinker region of the pUC19-derived DNA segment have been removed. The insert of the 0.8 kb Taq I fragment containing the CAT gene contains a BamH I site next to one of Taq I sites, i.e. about 2.1 kb from the Hind III site closer to the deleted polylinker region. A 0.3 kb BamH I fragment (see FIG. 8E) containing CAE II has been inserted into this site. This construction placed the CAT gene downstream of the CAE I and upstream of the CAE II. Numbers in parentheses indicate the lengths in kilobase-pairs (in a clockwise direction) from the EcoR I site within the pUC19-derived segment of this plasmid.

FIG. 10 shows that the CAE II directs the production of defined 3'-ends of late mRNA. RNAs were extracted from cells infected with either: (A) recombinant vaccinia virus (A394) containing the CAT gene under the control of CAE I; or (B) recombinant vaccinia virus (A415) containing the CAT gene under the control of both CAE I and CAE II. The RNA's were resolved by electrophoresis in a 1% agarose gel containing 2.2M formaldehyde. The RNAs were then transferred from the gel to nylon membranes as described in Example VII. [$^{32}$p]-labelled probes specific for the coding sequence of the CAT gene were hybridized with the immobilized RNA on the membrane. After hybridization the labelled DNA/RNA hybrids were visualized by autoradiography. The microdensitometer scans of the autoradiograms show that CAT-gene-containing mRNAs of heterogeneous length are produced by recombinant A394, whereas (CAT-gene-containing) mRNAs of a defined length are produced by the recombinant A415, which contains the CAT gene under the control of both CAE I and CAE II.

DESCRIPTION OF THE PREFERRED EMBODIMENTS

Figure 3A:
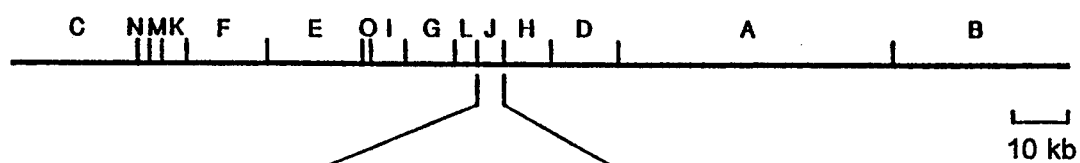
Figure 3B:

The invention comprises modified viral nucleotide sequences and their use to direct the expression of genes cloned into poxvirus-derived vectors. These viral sequences (defined as cis-acting elements) appear to control the transcription of a strongly-expressed gene (the 160K gene) of cowpox virus. In addition, they appear to determine the nature of both the 5'- and the 3'-ends of the gene's mRNAs. The structures of the 5'- and 3'-ends of a mRNA are important because they will probably affect the rate at which the mRNA is degraded. Also, the structure of the 5'-end of the mRNA is important because it will affect the efficiency with which the mRNA is translated. Thus, there are several ways in which these cis-acting elements may control the level of expression of a cloned gene.

The modified cis-acting elements have been placed into an insertion vector that facilitates the insertion of these elements, together with the coding region of a cloned gene, into the genome of poxviruses. This process is mediated by homologous recombination, and it requires that the elements and cloned gene are not inserted into an essential part of the genome. In the described examples, the insertion vector consists of an E. coli plasmid vector (pUC19) containing the Hind III J fragment of the DNA of the western reserve strain of vaccinia virus. The cis-acting elements and cloned genes have been inserted into the thymidine kinase (tk) gene within the Hind III J fragment. Insertion inactivates the tk gene. As a result, the replacement of the viral tk gene (in the genome of a poxvirus) with the interrupted tk gene of the insertion vector, generates a tk− recombinant virus that enables selection of recombinants having the inserted DNA. Alternatively, the cloned gene and the cis-acting elements may be inserted into another nonessential region of the DNA of the vaccinia virus or another poxvirus.

The significant feature of this process is that the expression of the hybrid gene, consisting of the cloned gene fused to the cis-acting elements derived from the 160K gene, retains the desirable characteristics of the expression of the 160K gene. It is clear that the essential cis-acting portions of the segments designated CAE I and CAE II may comprise one or more shorter sequences within CAE I and CAE II that by effecting enhanced translation, transcription and/or some other process act to cause the increased product levels of the invention. It may also well be the case that other portions of CAE I and CAE II play no role in the increased levels of the invention and may be omitted.

In the present invention, a cloned gene is expressed by combining the cis-acting regulatory elements derived from the 160K gene with the coding region of the cloned gene. The unmodified cis-acting element I shown in FIG. 1 directs the transcription and also determines the 5'-terminal structure of the mRNA. The modifications of this sequence comprise insertion of endonuclease restriction sites to facilitate both the appropriate insertion of the elements into the insertion vector, and the insertion of cloned genes such that they are under the control of the modified cis-acting elements.

As described in more detail in the examples below, a p1200 insertion vector has been constructed as a preferred embodiment of this invention. This construction employs the Brighton red strain of cowpox virus (obtained from the American Type Culture Collection, ATCC VR-302) and the western reserve strain of the vaccinia virus (obtained from Dr. W. K. Joklik, Duke University Medical Center, Durham, N.C.; an alternative source of this virus is the American Type Culture Collection, virus ATCC VR-119). Although these strains are employed in the examples, other strains and species of virus may be used that perform the particular functions of these strains, that is: (1) acting as a recombinant virus capable of infecting the desired host or cells; (2) providing the DNA fragment that is used to mediate homologous recombination between the insertion vector and the DNA of the virus; and (3) acting as a source of cis-acting elements derived from a gene encoding a major ATI protein.

The p1200 vector is made by inserting a vaccinia DNA fragment, having sites for facilitating homologous recombination, into a pUC19, an E. coli plasmid cloning vehicle (Example II). In this process, the DNA of this vehicle is ligated to a purified fragment of vaccinia virus DNA (to generate p1133). This fragment of DNA mediates the insertion of the plasmid-contained DNA into the DNA of the virus. The cis-acting region (CAE I) upstream of the coding region of the 160K cowpox virus gene is mutagenized so that it contains certain endonuclease restriction sites (Example III). The modified CAE I element in the resultant plasmid is cut with Taq I and ligated into the Cla I site within a p1133 vector. The product of ligation is used to transform E. coli cells (Example IV). A plasmid containing the modified CAE I element is selected for use as the insertion vector (Example V). Plasmid p1245, containing CAE I and the chloramphenicol acetyltransferase (CAT) gene, is inserted into the DNA of the vaccinia virus in virus-infected tissue culture cells (Example VI). In another preferred embodiment of the invention, the cis-acting element, CAE II, is inserted downstream of the CAE I/CAT gene section (Example VII). It is important that the downstream cis-acting element is aligned in the appropriate orientation such that transcription of the cloned gene may continue into this element and produce a distinct 3'-end to the messenger RNA. Although only employed with CAE I in the examples, it is probable that CAE II will function independently of CAE I, and will function when placed downstream of another promoter-functional or other upstream transcriptional regulatory sequence in a poxvirus-derived vector.

The plasmid containing the coding region of a cloned gene ligated to the modified viral regulatory sequence is prepared and purified using standard techniques as described below. Cells infected with vaccinia virus or another poxvirus are transfected with the plasmid under conditions to enable homologous recombination between the insertion vector and the viral genome. This results in the insertion of the regulatory sequences and cloned gene of the plasmid into the poxvirus genome.

The CAT gene used in the examples of the invention may be replaced by any DNA that encodes a desirable product, including, but not limited to, viral, mammalian, avian and bacterial DNA, thus allowing enhanced production of any of these products through infection of the chosen cells or organism by recombinant infectious viruses containing the selected gene and the elements of the invention as described. This DNA could be a DNA copy of an RNA or part of an RNA.

Identification of cells in which the appropriate recombination has occurred may be by inactivation of markers located in the DNA at the site of the insertion. Other standard genetic identification techniques, such as: (1) characterization of the DNA itself through hybridization analyses; or (2) identification and characterization of the protein product itself, may also be used.

This invention will be more clearly understood by reference to the following examples, which are not to be construed as limiting the invention.

EXAMPLE I

Definitions of the Cis-acting sequence elements involved in the production of the mature mRNAs of the 160K cowpox virus gene.

The nucleotide sequence at the beginning of the coding region of the 160K gene shown in FIG. 1. This cis-acting element will be referred to as cis-acting element I or CAE I. The nucleotide sequence responsible for the generation of the defined 3'-end mRNA of the 160K gene is shown in FIG. 2. This will be referred to as cis-acting element II or CAE II. These cis-acting elements, one at the beginning and one at the end of the coding region of the 160K gene that encodes the ATI protein have been identified and isolated (Patel and Pickup, manuscript submitted (1987)).

EXAMPLE II

Insertion of the Hind III J Fragment of the DNA of Western Reserve strain of vaccinia virus, into the Hind III site of pUC19.

Vaccinia virus (VV) was cultured and purified as described by Joklik, *Virology* 18: 9–18 (1962). DNA was isolated from virus particles as described by Nevins and Joklik, *J. Biol. Chem.* 252: 6930–6938 (1977). Restriction endonucleases and other DNA-modifying enzymes were obtained from either New England Biolabs, Inc. (Beverly, Mass.) or Boehringer Mannheim Corp. (Indianapolis, Ind.). Detailed information on these enzymes may be found in the Annual Catalog published by New England Biolabs, Inc. These enzymes were employed in the reaction conditions suggested by these suppliers. A brief description of all plasmids used is presented in Table 1.

Initially, 5 ug of VV DNA was cleaved with the Hind III restriction enzyme (see FIG. 3). The products of this reaction were resolved by electrophoresis in a 0.7% agarose gel containing 0.04M Tris-acetate, 0.001M EDTA, pH 7.9 (E buffer). DNA fragments were stained with ethidium bromide (0.5 ug/ml in water) for 20 minutes, and then visualized by illumination with ultraviolet light. The Hind III J fragment of the viral DNA was purified from the gel according to the method of Vogelstein and Gillespie, *Proc. Natl. Acad. Sci. USA* 76: 615–619 (1979).

A 5 ug quantity of the DNA of plasmid vector pUC19 (Yanisch-Perron et al., Gene 33: 103–119 (1985)) was cleaved with Hind III. Subsequently protein was removed from the DNA by phenol/chloroform extraction as described Palmiter, *Biochemistry* 133: 3606–3615 (1974). The DNA was ethanol-precipitated, and resuspended in 10 ul of 10 mM Tris-HCl, pH 7.4. The terminal 5' phosphate groups at the Hind III-generated ends were removed by treatment with calf intestinal alkaline phosphatase as described by Ullrich et al., *Science* 196: 1313–1319 (1977). After phenol/chloroform extraction, and ethanol precipitation, the phosphatased DNA was electrophoresed through a 0.7% agarose gel containing E buffer. The 2.7 kb linearized pUC19 DNA was then extracted from the gel, according to the method of Vogelstein and Gillespie, *Proc. Natl. Acad. Sci. USA* 76: 615–619 (1979). This step was done to remove uncut DNA from the cut, linearized DNA.

The phosphatased, linearized pUC19 DNA was ligated to the purified Hind III J fragment of VV DNA under standard reaction conditions as described by Dugaiczyk et al., *J. Mol. Biol.* 96: 171–184 (1975). After ligation, the DNAs were introduced into *E. coli* JM103 (Messing et al., *Nucl. Acids Res.* 9: 309–321 (1981)) by means of the CaCl$_2$ transformation procedure described by Mandel and Higa, *J. Mol. Biol.* 53: 159–162 (1970). Transformants containing the plasmid that contained the inserted DNA fragment were selected by their resistance to ampicillin, and their inability to produce the N-terminal portion of beta-galactosidase that would allow active beta-galactosidase to be produced within the cell.

Single colonies of the *E. coli* bacteria that were ampicillin resistant and lacked the ability to produce beta-galactosidase were cultured. Plasmid DNAs were extracted from these cultures by the rapid alkaline extraction method of Birnboim and Doly, *Nucl. Acids Res.* 7: 1513–1523 (1979). The DNAs were digested with Hind III, and the products were analyzed by electrophoresis in a 0.7% agarose gel. One recombinant plasmid (p1133) containing an intact Hind III J fragment was further characterized by cleavage with an enzyme (EcoR I) that cleaves the Hind III fragment of pUC19 and the Hind III J fragment of VV DNA asymmetrically. This enabled the orientation of the inserted fragment relative to the vector DNA to be determined.

Similar standard methods were employed to obtain all other recombinant plasmids. Large-scale preparations of plasmid DNAs were made according to the methods of Marko et al., *Anal. Biochem.* 121: 382–387 (1982).

EXAMPLE III

Oligonucleotide-directed mutagenesis of CAE I.

The nucleotide sequence at the initiation codon of the 160K gene was changed by the oligonucleotide-directed mutagenesis procedures of Carter, et al., *Nucl. Acids, Res.* 13: 4431–4443 (1985), as follows:

```
     690                710
     TAAATGGAGGTCACGAACCTT
``` to:

```
         *             *
     TAAATCGAGGTCACGAAGCTT
       Taq I          Hind III
```

The * indicates altered nucleotides. The numbers correspond to the numbers of the nucleotides as shown in FIG. 1.

This mutagenesis was done as follows. The 36-mer oligonucleotides 3'-ATT TAG CTC CAG TGC TTC GAA TAA CTT TTT ACA TGG-5' were synthesized on an Applied Biosystems 380A DNA synthesizer by the phosphoramidite method of Beaucage and Caruthers, *Tethradedron Letters* 22: 1859–1862 (1981). These were then purified by reverse-phase high-pressure liquid chromatography as described by Fritz et al., *Biochemistry* 17: 1257–1267 (1978). The selection primer SEL 2 (5'-CAC TAG AAT GTC ATC GAG G-3') was prepared in the same way.

Figure 4A:
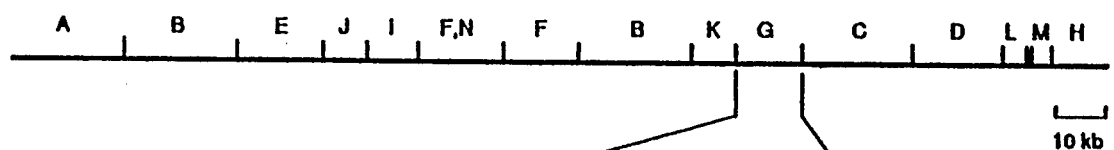
Figure 4B:
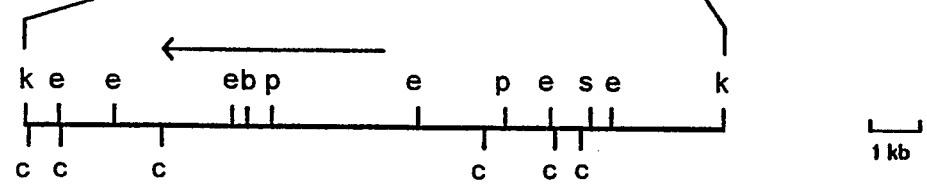
Figure 4C:
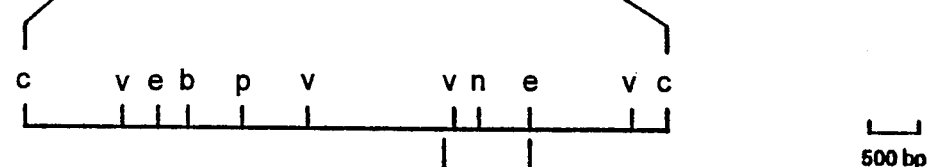
Figure 4D:
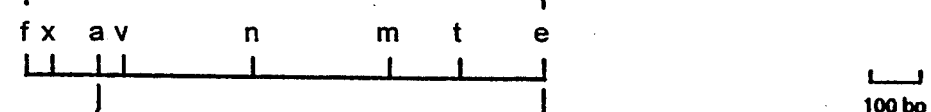
Figure 4E:
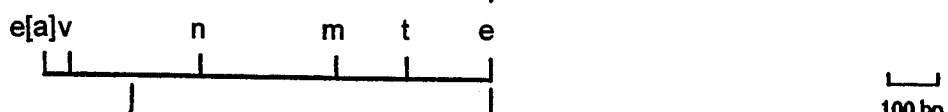

The substrate for the mutagenesis was prepared as follows: First, DNA of a plasmid (p2025) containing the 160K gene, including the DNA whose sequence (CAE I) is presented in FIG. 1, was digested with Acc I. The procedure described by Goodman and MacDonald, *Methods Enzymol.* 68: 75–90 (1979) was used to attach EcoR I linkers (5'-GGAATTC-3') to the Acc I generated ends. The single-stranded Acc I ends were converted to flush-ends by repair with the *Escherichia coli* DNA polymerase I (Klenow Fragment) obtained from Boehringer Mannheim. This procedure placed an EcoR I site at the position of the Acc I site (nucleotide 886) in the sequence shown in FIG. 1. The DNA was digested with EcoR I and the EcoR I fragment corresponding to nucleotides 1–886 (FIG. 1) was resolved by agarose gel electrophoresis. It was purified from the gel by the freeze-squeeze method of Thuring et al., *Anal. Biochem.* 66: 213–220 (1975). The 886 bp EcoR I fragment was inserted into the EcoR I site in the DNA of plasmid vectors pUC9 (Vieira and Messing, *Gene* 19: 269–276 (1982)). The plasmid containing this EcoR I fragment was designated p2030 (FIG. 4E).

The 886 bp EcoR I fragment was excised from p2030 and inserted into the EcoR I site within the replicative-form DNA of the mutagenesis vector m13MK19 (Carter et al., *Nucl. Acids Res.* 13: 4431–4443 (1985)). After ligation, the DNAs were transfected into TG1 cells. Id. Recombinant phage containing the insert were selected by screening for phage incapable of directing the synthesis of the N-terminal portion of the B-galactosidase protein. Phage containing the EcoR I fragment in the appropriate orientation were identified by the hybridization method described by Barnes (in *Genetic Engineering*, eds. Setlow, J. K., and Hollaender, A., Plenum, New York, Vol. 2, 185–200, 1980). Single-stranded DNAs of phage M13 vectors containing DNA complementary to the sequence shown in FIG. 1 were used as the hybridization probe. To perform this assay, first individual m13MK19 recombinant phages containing inserts were isolated from well-separated plaques in a lawn of *E. coli* TG1 cells (Carter et al., *Nucl. Acids Res.* 13: 4431–4443 (1985)). The phages were cultured, and single-stranded DNAs were prepared from them according to the method of Sanger et al., *J. Mol. Biol.* 143: 161–178 (1980). 0.1 ug of the probe DNA was hybridized with 0.1 ug of the DNA of each phage m13MK19 recombinant, in 10 ul of 0.3 M NaCl, 10 mM Tris-HCl (pH 7.5), 0.1 mM EDTA, for 2 hours at 65° C. Then the DNAs were electrophoresed through a 0.7% agarose gel containing E buffer. DNAs containing complementary inserts hybridized to form structures containing two covalently-closed single-stranded DNAs joined by a base-paired region of complementarity. The electrophoretic mobility of these dimers was considerably less than either of its component monomers. Consequently, the hybridizing DNAs were readily detected by comparison of the electrophoretic mobilities of the products of the DNA hybridizations with the electrophoretic mobilities of the monomer DNAs. In this way, an m13MK19 recombinant (designated M30/14A) containing the appropriate orientation of the 886 EcoR I fragment (i.e, complementary to the 36-mer mutagenic oligonucleotide) was isolated.

Single-stranded DNA of phage M30/14A was prepared by the method of Sanger et al., *J. Mol. Biol.* 143: 161–178 (1980), with the modifications of Carter et al., in *Oligonucleotide Site Directed Mutagenesis in M13*, Anglian Biotechnology Limited, Colchester, England (1985) and as described herein. After inoculation with phage, the cultures of TG1 cells were incubated for 6 hours. Phage particles were precipitated from 1 ml of the clarified growth medium by the addition of one-fifth volume of 2.5M NaCl and 20% polyethylene glycol (6000). The precipitate was allowed to form for 15 minutes at room temperature. The precipitated phage particles were centrifuged (5 minutes, 16,000×g, in an Eppendorf microfuge) and then resuspended in 100 ul of 10 mM Tris-HCl (pH 8.0) and 0.1 mM EDTA. 5 ul of a 10 mg/ml pancreatic RNAase (Boehringer Mannheim) in 10 mM Tris-HCl (pH 7.5) and 15 mM NaCl (previously heated to 100° C. for 15 minutes in this solution in order to inactivate any contaminating DNAase) was added to the solution containing the DNA. This was then incubated at 37° C. for 30 minutes. The DNA was extracted by the phenol/chloroform procedure of Palmiter, *Biochemistry* 133: 3606–3615 (1974). The extracted DNA was ethanol-precipitated, then resuspended in 10 mM Tris-HCl (pH 8.0) and 0.1 mM EDTA at a concentration of 1 ug/ml (1 unit of optical density/ml at 260 nm is equivalent to 40 ug/ml). This DNA was used as the template for the oligonucleotide-directed mutagenesis.

The mutagenesis was done in the following way. First, the oligonucleotides (both the 36-mer mutagenic primer and the selection primer SEL 2) were kinased according to the method of Weaver and Weissman, *Nucl. Acids Res.* 7: 1175–1193 (1979). Each reaction contained 100 pmoles of oligonucleotide, and 5 units of polynucleotide kinase, in 20 ul of a buffered solution containing 50 mM Tris-HCl (pH 8.0), 10 mM MgCl$_2$, 5 mM dithiothreitol (DTT), and 1 mM ATP. The mixture was incubated for 30 minutes at 37° C.

Next, the kinased oligonucleotides were annealed to the M30/14A substrate DNA under the following conditions: 10 pmol mutagenic oligonucleotide, 10 pmol of SEL 2 oligonucleotide, and 1 ug of single-stranded M30/14A DNA in 10 ul of 10 mM Tris-HCl (pH 8.0) and 10 mM MgCl$_2$. This mixture was heated to 80° C. and then allowed to cool to room temperature (about 30 minutes).

Extension and ligation of the oligonucleotides was achieved by adding: 1 ul of 100 mM Tris-HCl (pH 8.0), 100 mM MgCl$_2$; 1 ul of a mixture containing 5 mM dATP, 5 mM dGTP, 5 mM dCTP, and 5 mM TTP; 1 ul of 5 mM ATP; 1 ul of 100 mM DTT;; 2 ul of T4 DNA ligase (5 units/ul, Boehringer Mannheim) and 5 ul of *E. coli* DNA polymerase I, Klenow fragment (Boehringer Mannheim) at a concentration of 0.2 units/ul. Incubation was for 4 hours at 12°–15° C.

The sample was made up to a volume of 50 ul with 10 mM Tris-HCl (pH 8.0) and 10 mM EDTA. Competent *E. coli* cells, HB 2154 (Carter et al., *Nucl. Acids Res.* 13: 4431–4443 (1985)) were transformed with aliquots of this DNA by the CaCl$_2$ procedure described by Mandel and Higa, *J. Mol. Biol.* 53: 159–162 (1970). The HB 2154 is a repair-deficient strain of *E. coli* that contains the Eco K restriction-modification system. The transformed HB 2154 cells were diluted out and plated out in a lawn of *E. coli*, HB 2151 (Carter, et al., *Nucl. Acids Res.* 13: 4431–4443 (1985)). The HB 2151 cells also contain the Eco K restriction-modification system, but they are capable of repair functions. In this way, exposure of the phage DNA to repair—deficient (mutator) cells was minimized. The SEL 2 oligonucleotide was included to convert the oligonucleotide-primed DNA from a template-directed Eco K-site containing DNA to an Eco B-site containing DNA. Thus, progeny phage whose DNA had incorporated the SEL 2 oligonucleotide would be able to replicate in cells containing the Eco K restriction-modification system. Progeny phage whose DNA derived from the template strand of M30/14A would be expected to retain the Eco K site. These phage would be unable to replicate in cells containing the Eco K restriction-modification system. This selection system permitted some enrichment for progeny phage that contained the desired alterations in their DNA.

DNA hybridization procedures were used to identify the phages that had the altered sequences. The method used was essentially a modification of that described by Grunstein and Hogness, *Proc. Natl. Acad. Sci. USA* 72: 3961–3965 (1975), as in the following description. Although the M13 phage does not lyse its cells, it does produce plaques that are areas of bacterial cell lawn in which the cells are less dense because the phage-infected cells grow more slowly than the uninfected cells. Therefore, M13 phage-infected cells can be picked from plaques, and subsequently grown as bacterial colonies on plates of L-broth agar. About 100 colonies of M13 phage-infected cells were inoculated in an asymmetric grid-arrangement on L-broth agar plates. After 16 hours growth at 37° C., a nitrocellulose filter was placed on top of the colonies for 1 minute. The filter was removed and placed (colony-side face upright) on the surface of 500 ml of 0.5M NaOH. After 1 minute, the filter was immersed in this solution and left there for 5 minutes. The filter was removed, and placed on Whatman 3MM paper (obtained from American Scientific Products, Chicago, Ill.) to remove excess 0.5M NaOH. The filter was then immersed in 500 ml 0.5M Tris-HCl (pH 7.4) for 5 minutes. The filter was removed, blotted on Whatman 3MM paper, and then placed in another 500 ml of 0.5M Tris-HCl (pH 7.4) for 5 minutes. The filter was removed, blotted and then rinsed in two separate baths of 2×SSC buffer (1×SSC is 0.15M NaCl, 15 mM Trisodium citrate (pH 6.8)). Next, the filter was air-dried, before it was sandwiched between two sheets of Whatman 3MM paper, and baked at 80° C. in a vacuum oven for 2 hours.

The 36-mer oligonucleotide was [$^{32}$P]-labeled at its 5'-end by the method of Weaver and Weissman, *Nucl. Acids Res.* 7: 1175–1193 (1979). The reaction mixture contained 30 uCi [$^{32}$P]-ATP (3000 Ci/mole), 10 pmole of oligonucleotide, and 10 units of polynucleotide kinase in 50 mM Tris-HCl (pH 8.0), 10 mM MgCl$_2$ and 5 mM dithiothreitol. This was incubated at 37° C. for 30 minutes. To separate the labeled oligonucleotide from the unincorporated [$^{32}$P]-ATP, the mixture was made up to 200 ul with TNE buffer (0.1M NaCl, 10 mM Tris-HCl, pH 7.5, and 5 mM EDTA) and applied to a 0.2 ml DEAE Sephacel (Pharmacia, Piscataway, N.J.)

column. It was washed with 10 ml of TNE, then eluted with 1 ml of 6×SSC buffer.

The nitrocellulose filter containing the blotted phage DNA was prehybridized in 4 ml of 6×SSC buffer containing 5×Denhardt's solution (1×Denhardt's solution is bovine serum albumin (Fraction V), polyvinyl pyrrolidone, and Ficoll, each at 0.2 mg/ml (all supplied by Sigma, St. Louis, Mo.)), and 50 ug/ml of boiled, sonicated salmon-sperm DNA at 50° C. for 16 hours. The labeled oligonucleotide probe was added to the solution. Hybridization was at 50° C. for 8 hours. The conditions for washing the blots to detect the presence of the nucleotide changes were as described in the method of Wood et al., *Proc. Natl. Acad. Sci. USA* 82: 1585–1588 (1985). The wash solution contained 3M tetramethylammonium chloride (Me4NCl), 50 mM Tris-HCl (pH 8.0), 2 mM EDTA, and 1 mg/ml sodium dodecyl sulphate (SDS). The filter was rinsed in the wash solution at room temperature. Next, it was washed twice in the Me4NCl wash solution for 20 minutes at 65° C. Then without allowing the filter to dry completely, it was exposed to film for 16 hours at −70° C. The autoradiogram of the filter showed that the probe hybridized to the DNA in all the colonies. Next, the filter was washed twice in the Me4NCl wash solution at 73° C. for 20 minutes, and the filter was again exposed to film. The autoradiogram showed that the probe now hybridized with the DNA of only a few colonies. This allowed the DNA containing the unaltered sequence (two mismatches with the oligonucleotide) and those containing the altered sequence (complementary to the entire mutagenic oligonucleotide) to be distinguished.

Phage was plaque-purified from a colony that showed positive hybridization with the mutagenic primer at the higher temperatures. The plaque-purified phage (850 2B) was cultured, and both replicative form (double-stranded DNA) and single-stranded DNA of this phage were prepared as described above. To confirm that the desired sequence alterations had been effected, the nucleotide sequence of this region was determined, essentially by the method of Sanger et al., *J. Mol. Biol.* 143: 161–178 (1980). The single-stranded DNA was used as the template, and the universal primer, 5'-TCCCAGTCACGACGT-3' described by Heidecker et al., *Gene* 10: 69–73 (1980) was used in this reaction. The universal primer was obtained from New England Biolabs, Beverly, Massachusetts. Reaction conditions, and subsequent procedures for polyacrylamide gel electrophoresis of the products were those described by Biggin et al., *Proc. Natl. Acad. Sci. USA* 80: 3963–3965 (1983). This analysis showed that the DNA of the recombinant contained both of the oligonucleotide-directed base changes.

Figure 4F:

The 135 bp Nco I-Hind III fragment (corresponding to nucleotides 570–704 in FIG. 1, where the Hind III site was that introduced by the mutagenic oligonucleotide) was excised from the DNA of phage 850 2B. This fragment was inserted between the Nco I and Hind III sites in plasmid 2030. The resultant plasmid (p2046) contained an EcoR I-Hind III insert (FIG. 4F) corresponding to nucleotides 1–709 (in FIG. 1), except where the oligonucleotide-directed changes had been effected.

EXAMPLE IV

Insertion of the modified CAE I element into plasmid p1133

The DNA of plasmid p2046 was cut with the restriction enzyme Tag I. The 533 bp Tag I fragment, corresponding to nucleotides 161–694 in FIG. 1, except that a Tag I site, TGCA, is at position 694, was resolved by electrophoresis in a 1.5% agarose gel containing E buffer. This DNA fragment was extracted from the gel by the freeze-squeeze method as described above.

The DNA of plasmid p1133 was cut at the single Cla I site, which is within the Hind III J fragment of the VV DNA. This Cla I site is in the coding sequence of the viral thymidine kinase (tk) gene and it is 738 bp from the Hind III site that is close to the tk gene (Weir and Moss, *J. Virol.* 46: 530–537 (1983). The Cla I-linearized p1133 was phosphatased and gel-purified as described above.

Figure 5:
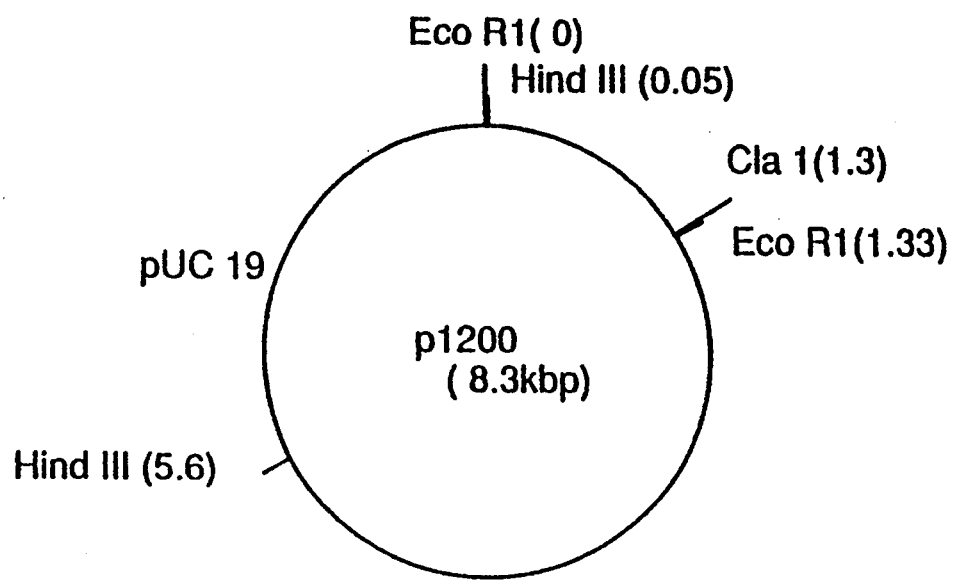

The purified 533 bp Taq I fragment of p2046 was ligated into the Cla I cut p1133 vector. Because of the nucleotide sequence of this fragment, only one Cla I site may be regenerated by the ligation of these Tag I-generated ends to the Cla I-generated ends. Thus, the joining of the Taq I-generated end corresponding to nucleotide 694 of the modified CAE I to either Cla I-generated end regenerates the Cla I site. But joining of the other Taq I-generated end to either Cla I site does not regenerate the Cla I site. The products of the ligation were used to transform *E. coli* JM103 cells, as described above. Plasmid DNA was extracted from a culture of the transformants. This DNA was cut with Cla I and electrophoresed in a 0.7% agarose gel containing E buffer. Linear molecules of DNA that were about 500 bp larger than the linearized p1133 DNA were extracted from the gel by the freeze-squeeze method. This linearized DNA was ligated back into monomer-form, covalently-closed circles, and then used to transform *E. coli* JM103. Plasmid DNA was extracted from colonies of individual transformants. These DNAs were cut with both Hind III and Cla I, in order to confirm that the plasmids contained the modified CAE I element. One of the plasmids (designated p1200) that contained the modified CAE I element in the orientation shown in FIG. 5 was selected for use as an insertion vector.

Use of the Cla I site in CAE I is convenient due to the ease of modifying the Taq I site to a single Cla I site. Other modifications placing another restriction endonuclease site at the appropriate CAE I site would also allow preparation and use of the vector of the invention for expression of high levels of products of the gene inserted downstream of CAE I.

EXAMPLE V

Insertion of the CAT gene downstream of the CAE I in the p1200 vector.

To demonstrate the ability of the CAE I in p1200 to direct high levels of expression of a cloned gene in mammalian cells, this vector was used to gain the expression of the bacterial chloramphenicol acetyltransferase (CAT) gene in human 143 cells. The 143 cells are a tk⁻ osteosarcoma derived cell line, Rhim et al., *Int. J. Cancer* 15: 23–29 (1975), provided by B. Moss, NIH, Bethesda, Md.; they are also available from the Human Genetic Mutant Cell Repository, Institute for Medical Research, Camden, N.J. (repository no. GM5887). This was achieved as follows.

A cloned copy of the chloramphenicol acetyltransferase gene of the *E. coli* transposable element Tn9 (Alton and Vapnek, *Nature* 282: 864–869 (1979)) was kindly provided by Dr. E. Linney (Duke Univ. Medical Center, Durham, N.C.). This copy, in plasmid p863, was a derivative of that in the plasmid pSV2-cat$^s$ described by Gorman et al., *Mol. Cell. Biol.* 2: 1044–1051

(1982). The Hind III-BamH I fragment containing the CAT gene had been cut from this plasmid. The ends of this fragment had been repaired with *E. coli* DNA polymerase 1 and multiple restriction sites (including Taq I sites) had been placed at each end of the promoterless coding region of the CAT gene. Cleavage of the DNA with the Tag I enzyme produced a fragment about 0.8 kb long which contained the entire coding region of the CAT gene. Furthermore, the initiation codon of the CAT gene was the first ATG triplet downstream of one of the Taq I sites. Because of this, and because Taq I and Cla I produce identical 5'-protruding single-stranded ends in their cleaved substrates, this 0.8 kb Taq I fragment was used to place the CAT gene downstream of the CAE I in p1200.

Figure 6:
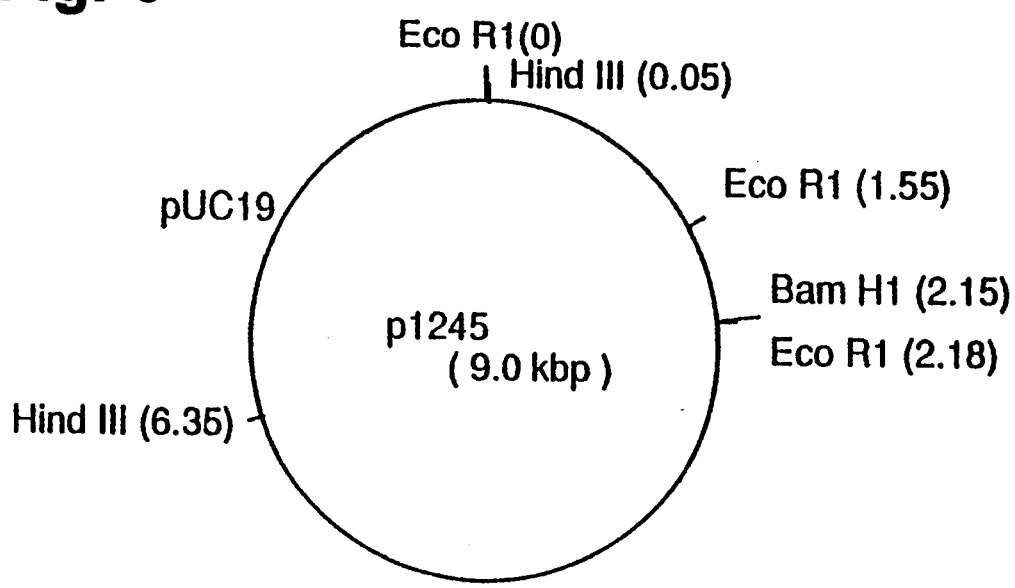

The p1200 DNA was linearized at its Cla I site, phosphatased and then purified by agarose gel electrophoresis as described above. The p863 DNA was cleaved with Taq I, and the 0.8 kb fragment containing the CAT gene was resolved by agarose gel electrophoresis. The DNA fragment was purified from the gel by the freeze-squeeze method. It was ligated into the Cla I site of p1200 DNA, and the products of the ligation were used to transform *E. coli* JM103 cells. Transformants were grown up as single colonies on L broth plates. L broth agar contains 10 g/l of tryptone, 5 g/l of yeast extract, 12 g/l agar (all obtained from Difco Laboratories, Detroit, Mich.) and 5 g/l of NaCl. Plasmid DNAs from these colonies were digested with EcoR I, and the EcoR I-generated fragments were resolved by electrophoresis in 1% agarose gels containing E buffer. Because the CAT gene contains an EcoR I site 220 bp from its initiation codon, the insertion of the CAT gene into p1200 provides a third EcoR I site in the recombinant plasmid. In addition, the asymmetric position of the EcoR I site within the CAT gene provides a simple means of identifying plasmids containing the CAT gene in the correct orientation relative to the CAE I in the p1200 vector. Thus, a plasmid containing the CAT gene in the appropriate orientation would be cleaved by EcoR I into three fragments of 6.9 kb, 1.5 kb, and 0.6 kb (FIG. 6). Colonies containing such a plasmid were identified. This plasmid was designated p1245.

EXAMPLE VI

Insertion of the CAE I/CAT gene hybrid into the DNA of the vaccinia virus

This was achieved by the method of Mackett et al., *Proc. Natl. Acad. Sci. USA* 79: 7415-7419 (1982), as follows: 2 ug of plasmid p1245 were cut with Hind III. The DNA was phenol/chloroform extracted and then precipitated in ethanol. The method of Graham and Van der Eb, *Virology* 52: 456-457 (1973) was used to prepare a calcium-phosphate precipitate of the Hind III cut p1245 DNA. The plasmid DNA together with about 20 ug of sonicated calf thymus DNA (Sigma Biochemicals, St. Louis, Mo.) was made up to 0.5 ml in sterile water. 0.5 ml of 2×Hepes buffered saline (HBS)(1×HBS contains 140 mM NaCl, 0.75 mM $Na_2HPO_4$, and 50 mM Hepes (pH 7.1) (Sigma Biochemicals) was mixed with the DNA solution. Next, 150 ul of 1M $CaCl_2$ was slowly added, and air was gently bubbled through the solution. The precipitate was allowed to form at room temperature for 45 minutes.

A preconfluent monolayer of $2 \times 10^6$ human 143 cells was infected with vaccinia virus at a multiplicity of 0.01 pfu per cell. The vaccinia virus used was a 3-times plaque-purified isolate of the Western reserve (WR) strain, containing a functional tk gene. The inoculum in 0.5 ml of modified Eagles minimal essential growth medium, MEM, supplemented with 3% fetal calf serum, FCS, (both from Gibco Laboratories, Grand Island, N.Y.) was allowed to adsorb to the cells for 1 hour at 37° C. Then, 10 ml of MEM containing 5% FCS was added to the cells.

After 1 hour of incubation at 37°, the 10 ml of growth medium was removed, and the 1 ml suspension of the calcium-phosphate precipitated DNA was added to the monolayer of tk⁻ 143 cells. After 30 minutes at room temperature, 10 ml of MEM containing 5% FCS was added, and the cells were incubated at 37° C. for 6 hours. The growth medium was then replaced with 1 ml of MEM containing 10% glycerol (Spandidos and Paul, *EMBO J.* 1: 15-20 (1982)). After 1 minute, the MEM (+glycerol) was removed, and the cell monolayer was washed twice with 10 ml of PBS (phosphate-buffered saline, i.e., 2.68 mM KCl, 1.47 mM $KH_2PO_4$, 0.137M NaCl, 8.06 mM $Na_2HPO_4$, pH 7.1) . Then, 10 ml of MEM containing 5% FCS was added and the cells were incubated at 37° C. for 48 hours. All incubations of mammalian cells in MEM media were done in an incubator that was constantly supplied with air containing 5% $CO_2$.

The transfected cells were harvested by two consecutive freeze-thaw cycles, which both dislodged the cells from the plastic surface of the flask and disrupted the cells. Virus and subcellular particles were disaggregated by a brief (1 minute) sonication in the cup horn unit of an ultrasonic cell disrupter (Model W380, Heat Systems-Ultrasonics, Inc., Farmingdale, N.Y.). A serial dilution of the virus suspension was made in PBS, and 0.2 ml aliquots were added to preconfluent monolayers of tk⁻ 143 cells (about $1 \times 10^6$ cells/monolayer) that had been cultured in MEM containing 5% FCS and 25 ug/ml 5-bromo-2'-deoxyuridine (BUdR, obtained from Sigma Biochemicals, St. Louis, Mo.). After a 1 hour adsorption period, 10 ml of MEM containing 5% FCS, and 25 ug/ml BUdR was added to each monolayer culture. These cultures were incubated at 37° C. for 48 hours. At this time, cultures containing about 50 plaques were harvested as described above. A serial dilution of the virus suspension was prepared and dishes that each contained about $10^6$ tk⁻ 143 cells were infected with 0.2 ml of a given virus dilution. After a 1 hour adsorption period, these monolayers were overlaid with MEM containing 5% FCS, 25 ug/ml BUdR, and 1% low gelling-temperature agarose (Sea plaque agarose, FMC Bioproducts, Rockland, Me.). These monolayers were incubated at 37° C. for 3 days. Individual plaques were visible without staining the cells. Several well-isolated plaques were identified. Cotton-wool plugged pasteur pipettes were used to extract plugs of agarose from above these plaques. The agarose plugs were each placed in 0.5 ml of sterile PBS, sonicated (as described above) for 30 seconds, and then used to inoculated a preconfluent monolayer of 143 cells. The infected monolayers were incubated at 37° C. for 3 days in MEM containing 5 % FCS and 25 ug/ml BUdR. The infected cells were harvested as described above, and stored at −70° C. These stocks were subsequently screened for the insertion of the hybrid CAT gene by DNA-hybridization analyses of viral DNA extracted from virus-infected cells.

DNA-hybridization analyses were done as follows. A monolayer of $2 \times 10^6$ 143 cells was infected with the plaque-purified recombinant virus at a multiplicity of infection of about 10 pfu/cell. Twenty-four hours after infection, the cells were scraped into the growth medium, and collected by low-speed centrifugation. The pellet of cells was resuspended in 0.9 ml of $H_2O$, followed by addition of 0.1 ml of 10×proteinase K buffer (0.2M NaCl, 10 mM $CaCl_2$, and 0.1M Tris-Cl at pH 8.0) containing 0.5 mg of proteinase K (Boehringer Mannheim, Indianapolis, Ind.). 50 ul of 10% SDS was added next. The suspension was mixed and incubated at 37° C. for 4 hours. Residual proteins were then removed by phenol/chloroform extraction as described above, except that mixing was achieved by slowly rocking the tube containing the DNA solution. Vigorous agitation of the mixture was avoided because it would have sheared the high molecular weight DNAs. The aqueous phase (containing the DNA) was dialyzed against 3 l of 10 mM Tris-HCl (pH 8.0) 1 mM EDTA for 16 hours at 4° C. The volume of the DNA solution after dialysis was about 1.0 ml. About 85 ul of the DNA solution was then digested with the restriction enzyme Hind III. To achieve this, first 5 ul of pancreatic RNAase (10 mg/ml, pretreated as described above to remove DNAase activity) was added, and the mixture was incubated for 15 minutes at 37° C. Next 10 ul of 10×Hind III buffer (0.5M NaCl, 0.5M Tris-HCl at pH 8.0, 0.1M $MgCl_2$, 1 mg/ml bovine serum albumin) and 5 ul of Hind III (20 units/ul) were added and the mixture was incubated at 37° C. for 3 hours to allow digestion. The Hind III-cut DNA was phenol/chloroform extracted, and then ethanolprecipitated. The precipitated DNA was resuspended in 10 ul of water. Then 10 ul of gel loading-buffer (2×E buffer containing 6% Ficoll (type 400)(Sigma Chemical Co., St. Louis, Mo.), 0.05% bromophenol blue and 0.1M EDTA) was added and mixed with the cut DNA. This DNA solution was heated to 65° C. for 5 minutes, and then rapidly cooled in ice water. To provide reference markers, a similar preparation of DNA was made from cells infected with the wild-type vaccinia virus (which does not contain any insert in its Hind III J Fragment).

The Hind III-cut DNAs from cells infected with the recombinant and wild-type viruses were then electrophoresed in a 0.7% agarose gel. Phage lambda DNA cut with EcOR I and Hind III was co-electrophoresed to provide size standards. The resolved DNA fragments were transferred from the gel to a nylon membrane (Biotrans, supplied by ICN Biomedicals, Irvine, Calif.) by the method of Southern, *J. Mol. Biol.* 98: 503–517 (1975).

A hybridization probe was produced by labeling the DNA of plasmid p1133 (pUC19 containing the Hind III J fragment of VV DNA, as described above, with [$^{32}$P]dATP by the nick-translation method of Rigby et al. *J. Mol. Biol.* 113: 237–251 (1977). A probe of phage lambda DNA was prepared in the same way. The probe was hybridized with immobilized DNA on the nylon filter according to the method of Southern, *J. Mol. Biol.* 98: 503–517 (1975). The nylon membrane was prehybridized in 20 ml of 6×SSC buffer containing 2×Denhardts solution and 400 ug of denatured, sonicated salmon-sperm DNA. The membrane and the prehybridization buffer were placed in a sealed plastic bag (from which the air had been expelled) and incubated at 68° C. for 16 hours. The prehybridization buffer was then replaced by the hybridization buffer, without letting the nylon filter become dry. The hybridization was done in 20 ml of 6×SSC buffer containing 1 mM EDTA, 0.1% SDS, 400 ug of sonicated, denatured, salmon-sperm DNA, 2×Denhardts solution, and 0.05 ug of denatured, [$^{32}$p] labeled hybridization probe (specific activity of about $1\times10^8$ cpm/ug). The hybridization was also done in a sealed plastic bag, with incubation at 68° C. for 16 hours. After the hybridization, the filter was washed in 500 ml of 2×SSC buffer containing 0.1% SDS, at 68° C. for 30 minutes. The wash step was repeated three times and then the filter was allowed to dry before it was placed against film. The autoradiogram of the membrane showed that the recombinant virus's Hind III J fragment had a lower electrophoretic mobility than that derived from the DNA of the wild-type virus. The shift in mobility corresponded to an increase in length of about 1300 bp, which is the length of the modified CAE I plus the CAT gene. Thus the DNA within the insertion vector had been introduced into the viral DNA. This recombinant virus was designated A394.

To determine whether or not the A394 recombinant directed the synthesis of enzymatically active CAT, a preconfluent monolayer of human 143 cells was infected with A394 virus at a multiplicity of 10 pfu/cell. In parallel, a monolayer of cells was infected with wild-type vaccinia virus and processed in exactly the same way as the cells infected with the A394 virus. Thirty-six hours after infection, the cells were scraped from the dish, and collected by low-speed centrifugation (about 200×g for 10 minutes at 4° C.). The cells were washed in PBS (at 4° C.), pelleted by a second centrifugation, and resuspended in 200 ul of 0.25M Tris-HCl, pH 7.5. This cell suspension was sonicated for 30 seconds in the cup horn sonicator in order to disrupt the cells. Cell debris was removed from the cell suspension by centrifugation for one minute, in an Eppendorf microcentrifuge (at 16,000×g). The supernatant was removed, and tested for CAT activity by use of the method described by Gorman et al., *Mol. Cell. Biol.* 2: 1044–1051 (1982). For these assays, acetyl coenzyme A (lithium salt) was obtained from Pharmacia, Inc., Piscataway, N.J., [$^{14}$C]-chloramphenicol (50–60 mCi/mmol) was obtained from Amersham Corporation, Arlington Heights, Ill., and silica gel thin-layer chromatography sheets (Baker-flex silica gel 1B2) were obtained from J. T. Baker Chemical Co., Phillipsburg, N.J. Each CAT assay mixture contained 7 ul of 10 mM acetyl coenzyme A, 5 ul of [$^{14}$C] chloramphenicol (about 0.25 uCi), 100 ul of 0.25M Tris-HCl (pH 7.5), and 20 ul of cell extract, made up to a final volume of 150 ul with water. Controls contained CAT (0.5 units; Pharmacia, Inc., Piscataway, N.J.) instead of the cell extract. The mixtures (without the acetyl coenzyme A) were incubated at 37° C. for five minutes before the acetyl coenzyme A was added to start the reaction. The reaction mixtures were incubated at 37° C. for 30 minutes, when each reaction was stopped by the addition of 1 ml of ethyl acetate (4° C.). The ethyl acetate was mixed well with the solution containing the CAT reaction mixture. This mixture was centrifuged for 30 seconds in an Eppendorf microfuge (at 16,000×g). The organic layer (containing the chloramphenicol) was dried and then resuspended in 20 ul of ethyl acetate. This was spotted onto silica gel thin-layer chromatography (TLC) sheets, and run with chloroform-methanol (95:5; ascending). The dried TLC sheet was exposed to film. The resolved acetylated forms of chloramphenicol were visualized by autoradiography. This assay demonstrated that the A394 recombinant directed the synthesis of active CAT; neither wild-type virus infected cells nor uninfected cells contained any detectable CAT activity.

To assess the level of expression of the CAT gene cloned under the control of the modified CAE I, the following assay was done. Preconfluent monolayers of human 143 cells ($2 \times 10^6$ cells/ monolayer) were infected with either wild-type vaccinia virus or recombinant virus A394 at multiplicities of 10 pfu/cell. The cells were incubated at 37° C. for 36 hours. Then they were scraped into their growth medium and collected by low speed centrifugation (about $200 \times g$ for 10 minutes at 4° C.). The cells were washed in PBS (at 4° C.), pelleted by a second centrifugation, and then resuspended in 400 ul of lysis buffer (50 mM Tris-HCl at pH 7, 10% glycerol, 5 mM EDTA, 1% SDS, 1 mM phenylmethylsulfonyl fluoride, and 25 mM DTT).

Aliquots (20 ul) of the cell lysate were heated to 100° C. for 3 minutes in order to solubilize and denature the proteins. The aliquots were then electrophoresed in a 15% polyacrylamide gel. The discontinuous buffer system described by Laemmli, Nature (London) 227: 680–685 (1970), was used in the electrophoresis. The following proteins were coelectrophoresed to provide size markers: trypsin inhibitor (soybean), 20,000 Daltons; lactate dehydrogenase (porcine muscle), 36,500 Daltons; glutamate dehydrogenase (bovine liver), 55,400 Daltons; phosphorylase b (rabbit muscle), 97,400 Daltons; and alpha$_2$macroglobulin (bovine plasma), 170,000 Daltons (reduced) and 34 0,000 Daltons (non-reduced) . These protein standards were obtained from Boehringer Mannheim, Indianapolis, Ind.).

Figure 7A:
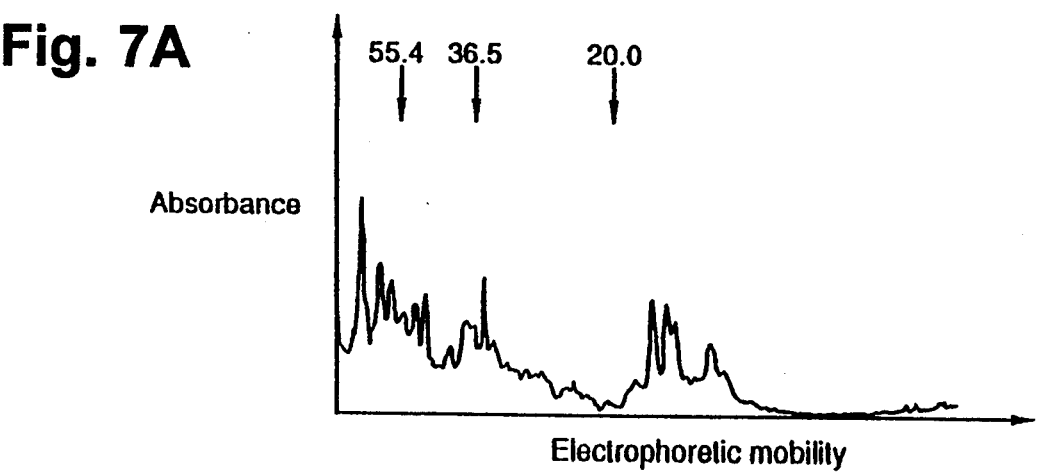
Figure 7B:
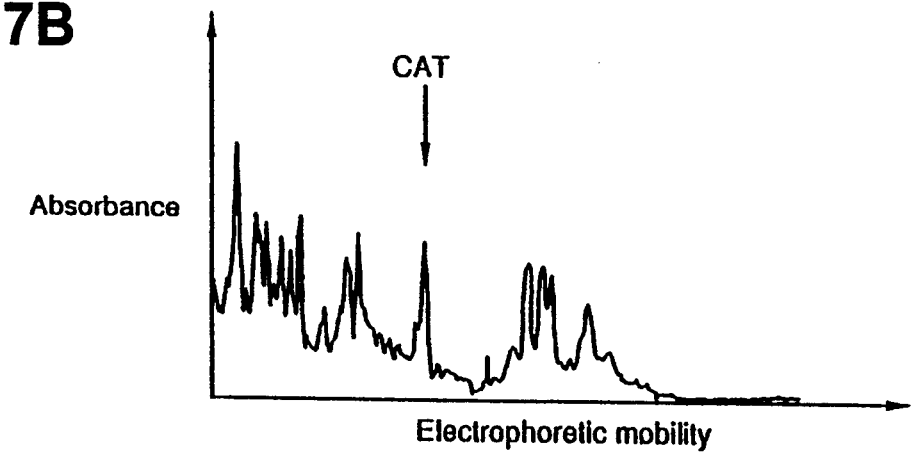
Figure 8A:
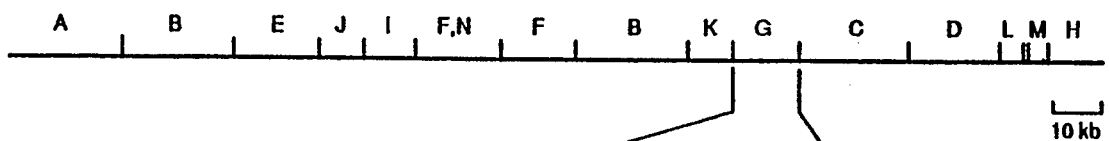
Figure 8B:
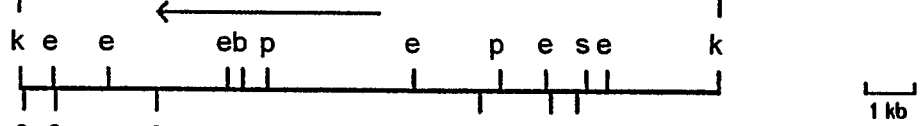
Figure 8C:
Figure 8D:
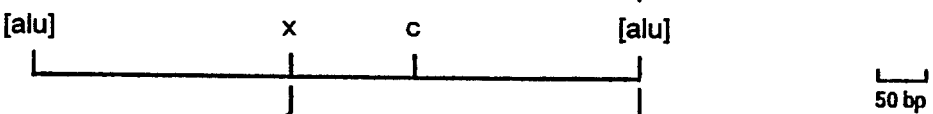
Figure 8E:

After electrophoresis, the proteins were visualized by staining with Coomassie brilliant blue R-250 (obtained from BioRad, Richmond, Calif.). Microdensitometer scans were made using a Zeineh scanning densitometer (Fullerton, Calif.). FIG. 7 shows microdensitometer scans of the polyacrylamide gel electrophoresis (PAGE) resolved polypeptides of: (a) cells infected with wild-type vaccinia virus; and (b) cells infected with the recombinant virus A394. The polypeptide profiles are the same except for one abundant polypeptide which is present in the lysate of cells infected with A394, but absent from cells infected with wild-type vaccinia virus. This A394-specific polypeptide has an apparent molecular mass of about 24 kDa; this polypeptide is the product of the cloned CAT gene.

Due to the well-known universality of the genetic code, this demonstration that a particular vector system allows expression of a bacterial gene in human cells, means that the products of genes of other organisms, such as mammalian or human genes, will also be formed by this vector system in human cells.

EXAMPLE VII

Insertion of CAE II downstream of the CAE I/CAT gene hybrid.

The scheme used to create the plasmid containing the CAE I/CAT gene/CAE II hybrid is outlined as follows. First, a derivative of pUC19 was made that lacked all polylinker cloning sites except the EcoR I and Hind III sites. This was prepared by cutting 10 ug of the pUC19 DNA at the EcoR I and Sph I sites. The Klenow fragment of the E. coli DNA polymerase 1 (Boehringer Mannheim) was used both to remove the protruding 3'-tail at the Sph I-generated end, and repair the 5'-tail produced at the EcoR I-generated end. To do this, the EcoR I-Sph I cut DNA was deproteinized by phenol/chloroform extraction as described above. The precipitated DNA was resuspended in 10 ul of 50 mM Tris-HCl (pH 7.5), 10 mM MgCl$_2$, 30 mM DTT, 2 mM ATP, 0.1 mM dATP, 0.1 mM dGTP, 0.1 mM dCTP, 0.1 mM TTP, containing 1 unit of DNA polymerase 1 (Klenow fragment). After 30 minutes at 21° C., 10 units of T4 DNA ligase (Boehringer Mannheim) were added. The mixture was then incubated for 4 hours at 21° C. to effect blunt-end ligation between the flush ends that had been produced at the Sph I and EcoR I-generated ends. This process removed the Sph I site and all sites in the polylinker region between it and the EcoR I site. The ligation of the repaired EcoR I-generated end to the flush-end at the Sph I site regenerated the EcoR I site. The products of the ligation were used to transform competent E. coli JM103 cells as described above. The transformants were plated out on L-broth plates containing ampicillin (25 ug/ml). Cultures were grown up from single colonies, and their plasmid DNA was examined by restriction enzyme analysis. Clones containing the plasmids that contained both the EcoR I site and the Hind III site, but lacked the other polylinker cloning sites were identified by agarose gel electrophoresis of the DNA products of digestion with these enzymes. One of these plasmids was designated p1247. This plasmid was used in subsequent constructions.

Next, the plasmid p1245 (containing the Hind III J fragment of VV DNA into which had been inserted the CAT gene under the control of the modified CAE I) was cut with Hind III. The Hind III fragment containing the CAE I/CAT gene was purified by agarose gel electrophoresis, and then inserted into the Hind III site of the plasmid p1247, according to standard methods described above.

The CAE II was derived from a 2 kb EcoR I fragment of the Kpn G I fragment of the DNA of cowpox virus (strain Brighton red). The map location of this fragment is shown in FIG. 8. This EcoR I fragment was subcloned from the DNA of plasmid p2003. Plasmid p2003 is plasmid vector pKBlll (Beckingham, Plasmid 4: 354–356 (1980)) into which had been inserted the Kpn I G fragment of the cowpox virus DNA. Methods used to culture the virus, purify the virus, extract its DNA, and then purify one restriction fragment were as described above in Example II, except that the cowpox virus was grown in monolayer cultures of human 143 cells, whereas vaccinia virus was grown in suspension cultures of mouse L929 fibroblast cells (available from the American Type Culture Collection, ATCC CCL1). The 2 kb EcoR I fragment containing CAE II was inserted into the EcoR I site of vector plasmid pUC19 to produce a plasmid designated p2060.

A 600 bp Alu I-generated restriction fragment containing CAE II (see FIG. 8D) was subcloned by standard methods described above, into the Hinc II site of plasmid vector pUC19.

Next, the 0.3 kb Xba I-generated fragment of p2070 containing CAE II was subcloned by standard methods into the Xba I site within the DNA of a plasmid designated p2050. The significant feature of p2050 is that it contains a BamH I restriction site derived from the pUC19 polylinker cloning sites at each side of the Xba I-generated cleavage site. Therefore, by cloning the 0.3 kb Xba I-generated fragment into the Xba I site of p2050, BamH I sites were attached to each end of the Xba I-generated fragment. An alternative method of achieving this would have been to add BamH I linkers [d(pCGGATCCG); commercially available from New England Biolabs, Beverly, Mass.] to the *E. coli* DNA polymerase I (Klenow fragment) repaired ends of the Xba I-generated fragment, according to the methods described above. The plasmid derivative of p2050, which contained the 0.3 kb Xba I fragment containing CAE II was designated p1274.

Figure 9:
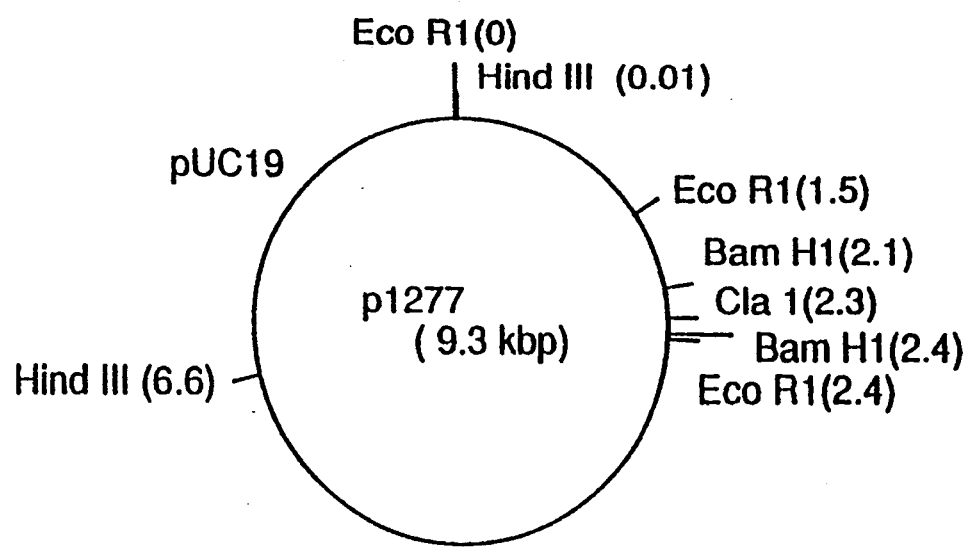

The 0.3 kb BamH I-generated fragment (containing CAE II) from p1274 was then subcloned by standard methods as described above into the single BamH I site in the DNA of plasmid p1275. Recombinant plasmids were screened for the correct orientation of CAE II relative to the orientation of the CAT gene by agarose gel electrophoresis analysis of the products of sequential EcoR I and cla I digestions of each plasmid DNA. A Cla I site is positioned asymmetrically within the CAE II. Thus, EcoR I-Cla I digests producing fragments of the following sizes would indicate an appropriate construct: 1.5 kb (EcoR I-EcoR I); 0.7 kb (EcoR I-Cla I); 0.1 kb (Cla I-EcoR I); and 6.9 kb (EcoR I-EcoR I)(FIG. 9). Bacteria containing a plasmid (p1277) whose DNA was cleaved by EcOR I and Cla I to such fragments were isolated. This plasmid is a derivative of the insertion vector plasmid p1200. In contains the CAT gene under the control of CAE I, and it contains the CAE II element, in the appropriate orientation relative to CAE I, downstream of the CAT gene.

The plasmid p1277 was used to insert the CAE I/CAT/CAE II hybrid gene into the genome of the vaccinia virus. The procedure described in Example VI was used to effect this insertion. The vaccinia virus recombinant containing the hybrid gene was designated A415.

The following procedure was used to determine that the CAE II was directing the production of a defined 3'-end in the mRNA of the CAT gene. A preconfluent monolayer of human 143 cells ($2 \times 10^7$ cells) was infected with recombinant virus A415 at a multiplicity of infection of 5 pfu/cell. A second preconfluent monolayer of cells was infected with recombinant virus A394 (also at a multiplicity of 5 pfu/cell). A third preconfluent monolayer of cells was infected with wild-type vaccinia virus (also at a multiplicity of 5 pfu/cell). Sixteen hours after infection at an incubation temperature of 37° C., each monolayer was washed once with 30 ml of PBS. Then the RNAs in these cells were extracted according to the method of Cox, *Methods Enzymol.* 12B: 120–129 (1968). The washed cells were lysed by the addition of 8 ml of 6M guanidinium HCl in 0.1M NaOAc at pH 5.0 and 4° C. To shear the DNA in the lysate, each lysate was passed through a 22-gauge syringe needle four times. The RNA was precipitated by the addition of 0.5 volumes of absolute ethanol (2 hours at −20° C.). The RNA was then collected by centrifugation at $16,000 \times g$ for 10 minutes, washed with 70% ethanol, and finally resuspended in 20 ul of water that had been treated with diethyl pyrocarbonate (obtained from Sigma Biochemicals, St. Louis, Mo.) to inactivate ribonucleases.

The purified RNAs were electrophoresed in a 1% agarose gel containing 2.2M formaldehyde according to the method described by Boedtker, *Biochim. Biophys. Acta*, 240: 448–453 (1971). The resolved RNAs were transferred to nylon membranes according to the method described by Southern, *J. Mol. Biol.* 98: 503–517 (1975). Fragments of phage lambda DNA were coelectrophoresed in the gel to provide size standards.

Figure 10A:
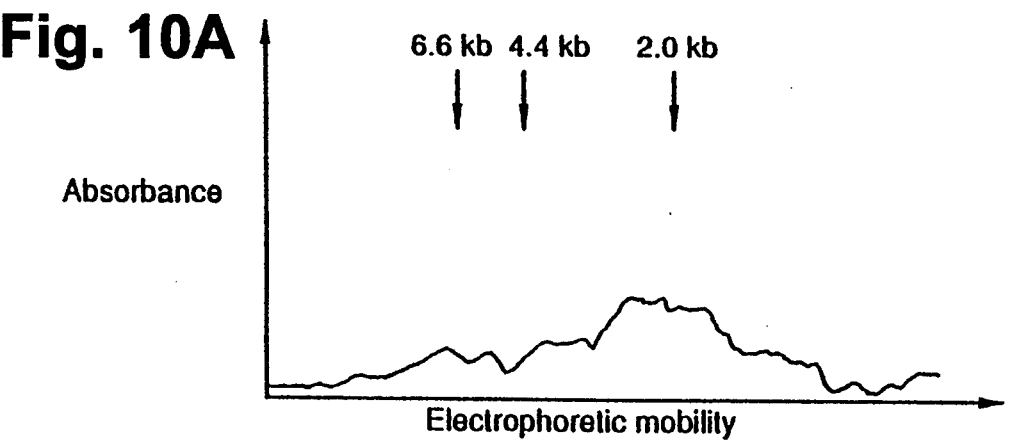
Figure 10B:
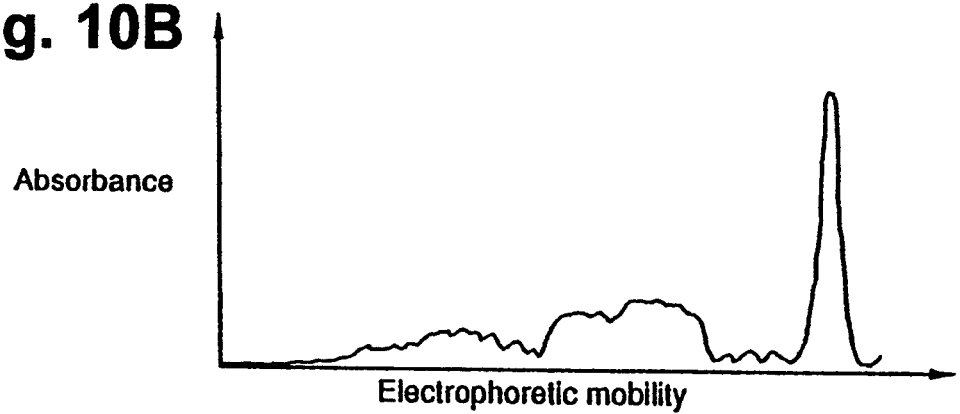

[$P^{32}$]-labeled DNA hybridization probes were made by nick-translation (as described above in Example VI) of phage lambda DNA and also plasmid p863 (a pUC19 vector containing the CAT gene insert). The lambda DNA probe was used to detect coelectrophoresed fragments that were used to provide the size standards. Hybridization conditions were as described by Maniatis et al., *Molecular Cloning: A Laboratory Manual*, Cold Spring Harbor, N.Y. (1982). After hybridization and washing, the dried filter was placed on photographic film. The autoradiogram of the film was scanned by a Zeineh scanning densitometer (Fullerton, Calif.). FIG. 10 shows scans of this autoradiogram. Panel A shows that the probe consisting of the CAT gene's nucleotide sequences hybridizes to mRNA that is heterogeneous in length. This mRNA is a product of the CAE I-CAT gene construct. Panel B shows that the probe consisting of the CAT gene's nucleotide sequences hybridizes to mRNA of a defined length: this RNA is a product of the CAE I-CAT-CAE II construct. Although CAE II is used in this example with CAE I, it is evident that CAE II may be used downstream from cloned genes in insertion/expression vectors with upstream DNA fragments other than CAE I.

As discussed above, other poxviruses also produce ATI proteins in significant quantities. Thus, although the above examples utilize cowpox ATI cis-acting elements, it is clear that cis-acting elements of the ATIs of other poxviruses, such as other orthopoxviruses and fowlpox virus, may be employed to provide vectors for use in the appropriate animal cells and to prepare vaccines for the appropriate hosts. It is also clear that, due to the similarity of various poxviruses, it is not necessary to use the same poxvirus source for the cis-acting elements as are used for the recombinant poxvirus containing the inserted cis-acting element and the cloned gene.

In addition to the disclosure of the examples discussed above, but derived from them, the essence of this invention may be used to construct an endogenous vector in a poxvirus genome for direct synthesis of a cloned gene rather than excising the CAE I and CAE II and constructing an exogenous vector as discussed in the examples. Thus, for example, nonessential regions of the 160K gene of the cowpox virus or its equivalent gene in the genome of other poxviruses may be replaced with a selected cloned gene placed in an insertion vector in which regions homologous to the regions flanking the gene for the ATI protein would flank the cloned gene. The result would be that the selected cloned gene would be inserted in and aligned between CAE I and CAE II in the endogenous vector, and would be expressed in high levels similar to those of the ATI protein. The viral host containing its own CAE I and CAE II and the inserted selected cloned gene could be utilized as is the recombinant vaccinia virus containing the CAE I, cloned gene and CAE II construct discussed in Example VII.

Exogenous vectors can also be used to produce a mRNA whose 5'-end is similar to that of the 160K gene (i.e., a poly(A) sequence immediately upstream of the initiation codon). To do this, another derivative of p1200 was constructed in which the Cla I site within the sequence TAAATCGAT was converted to a BamH I site, i.e., TAAATGGATCC. Briefly, this was done as follows: the DNA of plasmid p1275 (described above) was cut with Cla I. The resulting single-stranded tails were removed by digestion with the nuclease S1 under standard conditions (Vogt, *Eur. J. Biochem* 33: 192–200 (1973)). Then BamH I linkers were added to the ends by blunt-end ligation. The linkers employed were pGGATCC (which were chemically synthesized as described above). The advantage of this vector is that it should regenerate the exact leader sequence of the mRNA of the 160K gene, i.e., the poly(A) leader sequence together with the initiation codon.

TABLE 1

Brief descriptions of the various plasmids constructs used in Examples I–VII.

| Plasmid | Description |
|---|---|
| pUC9 | A cloning vector derivative of pBR322 (Vieira and Messing, Gene 19: 269–276 (1982)) |
| pUC19 | A cloning vector derivative of pUC9 (Yanisch-Perron et al., Gene 33: 103–119 (1985)). |
| p863 | Cloning vector plasmid pUC12 (Messing, Methods Enzymol. 101C: 20–78 (1983)) containing a cloned copy of the bacterial chloramphenicol acetyltransferase (CAT) gene derived from the plasmid pSV2-cat$^s$, described by Gorman et al., Mol. Cell. Biol. 2: 1044–1051 (1982). |
| p1133 | pUC19 containing at its Hind III site, the Hind III J fragment of the DNA of the WR strain of vaccinia virus. |
| p1200 | p1133 containing the 533 bp Taq I fragment (containing the modified CAE I) at the single Cla I site. The 533 bp Taq I fragment was obtained from p2046. |
| p1245 | Plasmid p1200 containing the CAT gene downstream of the modified CAE I. |
| p1247 | Plasmid pUC19 in which all restriction sites of the polylinker cloning sites have been deleted except the EcoR I and Hind III sites. |
| p1274 | Plasmid p2050 containing the 0.3 kb Xba I fragment (containing the CAE II of p2070 inserted at its Xba I site. |
| p1275 | Plasmid p1247 containing the modified CAE I within the Hind III J fragment of the DNA of vaccinia virus, the Hind III fragment being derived from p1245. |
| p1277 | Plasmid p1275 containing the 0.3 kb BamH I-generated fragment (containing CAE II) inserted at its BamH I site. This plasmid is a derivative of p1200 containing the CAT gene and then the CAE II downstream of the CAT gene. |
| p2003 | Plasmid cloning vector pKB111 (Beckingham, Plasmid 4: 354–356 (1980)) containing the Kpn I G fragment of the DNA of the Brighton red strain of cowpox virus. |
| p2025 | pUC9 containing the 6.4 kb Cla I fragment (containing the 160 K gene) of the Kpn I G fragment of the DNA of the Brighton red strain of cowpox virus. The 6.4 kb Cla I fragment was inserted into the Acc I site within the pUC9 DNA. |
| p2030 | pUC9 containing an 886 bp EcoR I fragment corresponding to nucleotides 1–886 (FIG. 1). This EcoR I fragment is the cis-acting element I (CAE I). |
| p2046 | p2030 containing a modified version of CAE I, i.e., pUC9 containing an EcoR I-Hind III insert corresponding to nucleotides 1–709 (Fig.1) except that oligonucleotide-directed mutagenesis procedures placed a Taq I site at nucleotide 693 and a Hind III site at nucleotide 704. |
| p2050 | A derivative of pUC19 plasmid containing an insert that places a BamH I site at each side of the Xba I site in its polylinker region. |
| p2060 | Plasmid pUC19 containing a 2 kb EcoR I fragment (of the cloned Kpn I G fragment in p2003) that contains CAE II. |
| p2070 | Plasmid pUC19 containing a 600 bp Alu I-generated fragment (containing CAE II) of the plasmid p2060. |

I claim:

1. A recombinant vector comprising:
    i) a vaccinia virus,
    ii) a 3' cis-acting element II (CAE-II) of a gene encoding the major component of a cowpox virus A-type inclusion body, and
    iii) a gene encoding a protein other than the major component of a cowpox virus A-type inclusion body;
    wherein said gene (iii) is present in said vaccinia virus (i) operably linked to and upstream of said CAE-II.

2. The recombinant vector according to claim 1 wherein said CAE-II has the following sequence:

```
AGC TTC GTC TTT TTA CCT CTA CAT CTA ACG GTT GCC
TTG TCC TGA GTT AAA TGC CTC AGA CGC AAG TAA TAA
ATT GGT CCA AAA AAT ACT TTG GAT GCA TAA GGC TTA
TCC GTT TCA GGA TCA TAG AGA ATC TTT TCA CAA AAG
ATT TTA TCC GAT AAT TCT TCA TCA GAC AAT TTC GGA
TTT GAA TGC TCA TAA CAT TGT TTA GCG AAT TGC ATA
TAT GTA TCG ATG GAT GTT TCG TTA CTA CTA GGA AAA
CAG ACA GGT CGG TTT TCT CCC TTA TTG TTG TAC GGC
TTA GCA GAA TAT GCG GCT GTT AAA ATA ACT TCT ATC
AAC ATA GAT ATA GTT TTT CTA GA.
```

3. A cultured cell comprising said recombinant vector according to claim 1.

4. The cell according to claim 3 wherein said cell is a mammalian cell.

5. The recombinant vector according to claim 1 further comprising a promoter operably linked to and upstream of said gene (iii).

6. A recombinant vector comprising:
    i) a vaccinia virus,
    ii) a 5' cis-acting element-I (CAE-I) of a gene encoding the major component of a cowpox virus A-type inclusion body,
    iii) a 3' cis-acting element-II (CAE-II) of a gene encoding the major component of a cowpox virus A-type inclusion body,
    iv) a gene encoding a protein other than the major component of a cowpox virus A-type inclusion protein,
    wherein said gene (iv) is present in said vaccinia virus (i) operably linked to and downstream of said CAE-I and operably linked to and upstream of said CAE-II.

7. A cultured cell comprising said recombinant vector according to claim 6.

8. The cell according to claim 7 wherein said cell is a mammalian cell.

9. A method of producing a protein comprising the steps of
    i) constructing a recombinant vector comprising:
       a) a vaccinia virus,
       b) a gene encoding said protein operably linked to a promoter, and
       c) a 3' CAE-II of a gene encoding the major component of cowpox virus A-type inclusion body,
    wherein said gene (b) is present in said vaccinia virus (a) operably linked to and upstream of said CAE-II;

ii) introducing said recombinant vector into a cultured cell; and iii) culturing said cell resulting from step (ii) under conditions such that said gene (b) is expressed and said protein thereby produced.

10. The method according to claim 9 wherein said recombinant vector further comprises a 5′ CAE-I of a gene encoding the major component of cowpox virus A-type inclusion body operably linked to and upstream said gene (b).

11. The method according to claim 9 wherein said cell is a mammalian cell.

12. A DNA fragment consisting of a 3′ cis-acting element II (CAE-II) of a gene encoding the major component of a cowpox virus A-type inclusion body.

* * * * *